United States Patent
Rahimi et al.

(10) Patent No.: US 10,987,390 B2
(45) Date of Patent: Apr. 27, 2021

(54) PLANT STEM CELL PRODUCT TREATMENTS

(71) Applicants: Maryam Rahimi, Long Beach, CA (US); Steven Phillip Gallagher, Chatsworth, CA (US)

(72) Inventors: Maryam Rahimi, Long Beach, CA (US); Steven Phillip Gallagher, Chatsworth, CA (US)

( * ) Notice: Subject to any disclaimer, the term of this patent is extended or adjusted under 35 U.S.C. 154(b) by 0 days.

(21) Appl. No.: 16/388,802

(22) Filed: Apr. 18, 2019

(65) Prior Publication Data

US 2020/0179275 A1 Jun. 11, 2020

Related U.S. Application Data

(60) Provisional application No. 62/776,237, filed on Dec. 6, 2018.

(51) Int. Cl.

| | |
|---|---|
| *A61K 9/127* | (2006.01) |
| *C12N 5/04* | (2006.01) |
| *A61P 11/00* | (2006.01) |
| *A61K 36/73* | (2006.01) |
| *A61M 11/04* | (2006.01) |
| *A61M 15/06* | (2006.01) |
| *A61K 36/18* | (2006.01) |
| *A61K 9/00* | (2006.01) |
| *A61K 9/16* | (2006.01) |
| *A61K 9/50* | (2006.01) |
| *A61P 35/00* | (2006.01) |
| *A61K 36/45* | (2006.01) |
| *A61K 36/898* | (2006.01) |
| *A61C 15/04* | (2006.01) |

(52) U.S. Cl.
CPC .............. *A61K 36/18* (2013.01); *A61K 9/006* (2013.01); *A61K 9/0056* (2013.01); *A61K 9/0073* (2013.01); *A61K 9/1273* (2013.01); *A61K 9/1647* (2013.01); *A61K 9/1652* (2013.01); *A61K 9/5026* (2013.01); *A61K 9/5036* (2013.01); *A61K 36/45* (2013.01); *A61K 36/73* (2013.01); *A61K 36/898* (2013.01); *A61M 11/04* (2013.01); *A61M 15/06* (2013.01); *A61P 11/00* (2018.01); *A61P 35/00* (2018.01); *C12N 5/04* (2013.01); *A61C 15/046* (2013.01)

(58) Field of Classification Search
CPC ...... A61K 9/0073; A61K 36/18; A61K 36/73; A61P 11/003; A61P 11/00
See application file for complete search history.

(56) References Cited

U.S. PATENT DOCUMENTS

| | | | | |
|---|---|---|---|---|
| 5,643,853 A | * | 7/1997 | Morre | A01N 31/02 504/130 |
| 2010/0215625 A1 | * | 8/2010 | Iida | A61K 36/185 424/93.7 |
| 2013/0327323 A1 | * | 12/2013 | Rubin | A61M 11/02 128/200.18 |

FOREIGN PATENT DOCUMENTS

CN 105816423 A * 8/2016 ............. A61K 47/02

OTHER PUBLICATIONS

Mark C. Ashma/Nebulizers and E-Cigs from "Welcome to the world's largest e-cigarette website: the voice of vaping since 2007". Web posting dates: Apr. 10, 2012; Apr. 12, 2012. Retrieved from the Internet on: Apr. 10, 2020 from URL<https://www.e-cigarette-forum.com/threads/ashma-nebulizers-and-e-cigs.286192/>. (Year: 2012).*

* cited by examiner

*Primary Examiner* — Amy L Clark

(57) ABSTRACT

Embodiments of the invention include plant stem cell products and treatment methods using the products. In some embodiments, the products may include extracts of plant stem cells, such as apple stem cells, and an aerosolizing device configured to create an aerosol from the plant stem cell products and to deliver the aerosol to the lung via inhalation. Treatment methods include aerosol inhalation of the plant stem cell products.

11 Claims, 10 Drawing Sheets

Figure 1:
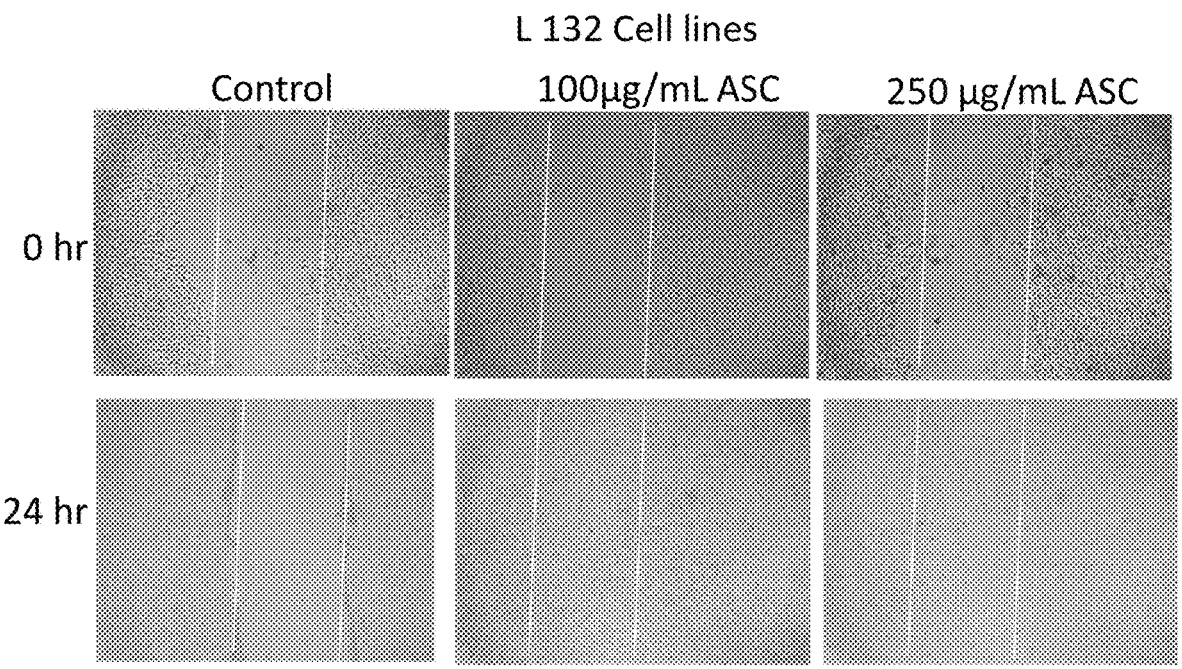

Acridine Orange/Ethidium Bromide Staining of Lung Cancer Cell Line A549

Acridine Orange/Ethidium Bromide Staining of Lung Cancer Cell Line NCI-H520

Calcein AM Staining in A549 Lung Cancer Cell Line

Calcein AM Staining in NCI-H520 Lung Cancer Cell Line

PLANT STEM CELL PRODUCT TREATMENTS

RELATED PATENT APPLICATION

This application claims the benefit of U.S. provisional patent application No. 62/776,237 entitled Aerosol treatments, filed on Dec. 6, 2018 by Maryam Rahimi. The entire content of this provisional patent application is incorporated by reference herein for all purposes.

TECHNICAL FIELD

This invention relates to treatment of disease conditions by application of plant stem cell products. In embodiments, the invention includes treatment of lung conditions by inhalation of aerosols including plant stem cell products.

BACKGROUND

Plant extracts form the basis of most traditional medical treatments. Active materials isolated from plant extracts, ranging from aspirin to morphine to paclitaxel to quinine form a large fraction of the modern pharmacopeia. The structural diversity of plant-derived compounds is enormous, and its exploration is still an active part of pharmaceutical development. Plants are the source of numerous compounds of therapeutic value in human disease. The major classes of plant-based medicines include alkaloids, glycosides, polyphenols and terpenes.

Multicellular plants, like animals, are composed of differentiated tissues and stem cells. Plant stem cells are dedifferentiated cells capable of division to create more stem cells and differentiated cells or their precursors. These replicating cells may be isolated from a part of a plant regenerating from an injury or the progeny of such cells. Injury sites may be from any portion of a plant such as callus, leaves, fruit, stems, flowers, roots, meristem, root cap, or seeds. Other plant stem cells may be derived from cells of a developing plant embryo, from a plant callus, or from plant tissue samples (explants) in tissue culture medium in vitro. Plant stem cells may be derived from many different cell types and may be able to differentiate into a whole plant. Plant stem cells, as used in this document, includes at least meristem cells, callus-derived cells, injury-site derived cells, and embryonic cells. Meristem cells at ends of stalks and in the root apex provide the plant with new cells and enable the plant to grow throughout its life. A callus is a stage of somatic embryogenesis (i.e. zygote formation without fertilization) followed by dedifferentiation producing stem cells capable of generating new plant tissue. The phrase plant stem cells as used herein includes extracts of such cells including products of stem cell lysis or partial digestion.

Differentiated plant cells produce a wealth of compounds evolved to combat predation, parasitism, disease, or adverse climatic conditions, to signal, or to encourage pollination or seed distribution. Differentiated plant cells such as roots, flowers, fruit, and seeds produce many of these compounds. However, plant stem cells by their nature lack the more specialized synthetic apparatus of differentiated cells. Instead, plant stem cells would be expected to focus more narrowly on producing materials needed to establish or replace other cell types, leaving the more diverse chemical synthesis tasks to specialized progeny. For example, plant stem cells in sprouting seeds, such as the germinated barley used in brewing, direct much enzymatic activity to producing simple sugars (such as the disaccharide maltose) to support the energy needs of a growing embryo.

Plant stem cells also have properties and functions that help stimulate and regenerate plants after injury and stress. This is most evident in the recovery from physical injuries such as in a wound or callus.

As in other eukaryotes including mammals, plant cells include telomeres that limit somatic cell division. Telomeres are ribonucleoprotein structures capping the ends of chromosomes. Telomeres shorten with each cell division, but telomerase, a reverse transcriptase, elongates telomeres in stem cells. Telomerase expression profiles mirror changes in telomere length, with the highest enzyme levels and telomere lengths associated with cells that have unlimited capacity for proliferation. Cells with reduced length telomeres undergo senescence or apoptosis. In large-bodied or long-lived animals, this process protects against somatic cell-derived cancers.

In vertebrates, telomeres are composed of 6-mer TTAGGG repeats coated with specific protecting proteins. Most plant telomeres (including model organism *Arabidopsis thaliana*) contain the 7-mer TTTAGGG that includes the vertebrate 6-mer. The *Arabidopsis*-type telomere is found in most angiosperms, but the sequence is absent in most monocot *Asparagales* species. Many species within *Asparagales* include the 6-mer TTAGGG sequence found in humans. Apparently, this sequence was altered during the rise of the *Asparagales*, an order including more than ten percent of all angiosperms. Onions (*Allium cepa*) are members of *Asparagales* and include the 12-mer telomere sequence CTCGGTTATGGG, which also includes the human 6-mer sequence.

Human tissue may be afflicted with a variety of diseases and conditions, such as injury, wounds, infection, inflammation, infarct, cancer, or diseases unique to specialized tissues. In some cases, these conditions may be treated by systemic administration of medications, including plant-derived medications. In other cases, these conditions may be treated by local administration of therapeutic agents to avoid unwanted effects outside the treated tissue or to limit the overall dosage.

Human lungs may be afflicted with a variety of disease or degenerative conditions. These include, for example, cancers, bronchial constriction, asthma, chronic obstructive pulmonary disease, emphysema, cystic fibrosis, inflammatory conditions, infections, and other conditions. Some lung conditions may be treated by direct administration of medications to the lungs via aerosol inhalation. In some cases, plant-based materials may treat some of these conditions.

For example, plants of the genus *Ephedra*, including *E. sinica* and others, produce the alkaloids ephedrine and pseudoephedrine in at least their stems and leaves. However, when taken systemically, extracts of *Ephedra* species have been associated with adverse cardiovascular and renal events and with anxiety, dizziness, difficulty urinating, dry mouth, headache, irritation of the stomach, nausea, psychosis, restlessness, sleep problems, and tremors. The FDA banned the U.S. sale of dietary supplements containing ephedrine alkaloids, as posing an unreasonable risk of injury or illness.

Flavonoids are polyphenolic compounds (a subclass of flavanols) in plant-based foods. Quercetin, a strong antioxidant, is the major food flavonoid. Quercetin can chelate metals, scavenge oxygen free radicals and prevent the oxidation of low-density lipoprotein (LDL). Oxidized LDL is an intermediate in the formation of atherosclerotic plaques. Quercetin might therefore contribute to the prevention of atherosclerosis: the intake of flavanols is inversely associated with subsequent cardiovascular disease in several prospective epidemiological studies. Epidemiological studies suggest that consumption of quercetin protects against cardiovascular disease, but its absorption in man is controversial. Feeding studies of plant-based foods in humans found quercetins from foods such as onions, which contain glucose conjugates of quercetin, were more readily absorbed than non-conjugated quercetins from apples or tea. Bioavailability of quercetin was about three times higher when the source contained glucose conjugates of quercetin. See Hollman et al. FEBS Lett. 1997 Nov. 24; 418(1-2): 152-6.

Lung conditions may be treated by aerosol inhalation as this may bring the treatment into direct contact with the affected tissue. The process of breathing delivers gases and inhaled materials directly to lug tissue, but the therapeutic effect of aerosolized therapies is dependent upon the dose deposited and its distribution. A drug or other treatment must be deposited past the oropharyngeal region to achieve therapeutic effectiveness in the lungs. The location of aerosol deposition, central or peripheral airways or alveolar, and the uniformity of distribution of the inhaled treatment may also play a role in the treatment's effectiveness.

Effectiveness of therapy may be compromised if an aerosol is delivered to a part of the lung devoid of the targeted disease or receptor. For example, autoradiographic studies have shown that receptors for the $\beta_2$ agonist albuterol are not uniformly distributed throughout the lung. These receptors are present in high density in the airway epithelium from the large bronchi to the terminal bronchioles. Airway smooth muscle has a lower $\beta_2$ receptor density, greater in the bronchioles than bronchi. However, more than 90% of all $\beta_2$ receptors are located in the alveolar wall, a region where no smooth muscle exists and whose functional significance is unknown.

Inhaled anti-inflammatory therapy is probably most beneficial when evenly distributed throughout the lung, since inflammatory cells, such as eosinophils, lymphocytes, macrophages, and dendritic cells, are present throughout the airways and the alveolar tissue in asthma.

It is an object of the invention to provide improved treatment systems and methods for disease states and conditions including lung conditions.

DISCLOSURE OF INVENTION/SUMMARY

I have discovered that plant stem cell extracts can be applied to human tissues to enhance regeneration, to prevent or reduce oxidative damage, to reduce inflammation, and to selectively kill cancer cells with relative sparing of normal cells.

In embodiments, the invention includes a system for treating a tissue of the body where the system includes a plant stem cell and a delivery device. The delivery device may be configured to deliver the plant stem cell product to an affected area of a body. In some embodiments, the tissue may be an internal tissue, that is, a tissue other than skin.

The delivery device may be any of an aerosolizing device, an injection device, a topical applicator, an eyedrop applicator, or an eardrop applicator. In some embodiments, the delivery device may be selected from a group consisting of a syringe having a hollow needle, an aerosolizing device, an eyedrop applicator, a condom, a buccal applicator, a suppository, an ingestible capsule, and an eardrop applicator.

An injection device may comprise a syringe and hollow needle sized for subcutaneous injection, for intradermal injection, for intramuscular injection, for intravenous injection, for intracapsular injection, intraarticular injection, for intraosseous injection, for intraperitoneal injection, for intracavernous injection, or for cardiac injection.

In some embodiments, the invention includes a system for treating a lung condition, where the system includes a plant stem cell product and an aerosolizing device. The device is configured to create an aerosol from the plant stem cell product and to deliver the aerosol to the lung via inhalation.

The plant stem cell may include one or more of a plant stem cell extract, a lyophilized plant stem cell, or an intact plant stem cell. The plant stem cell may also include an excipient, such as lactose, mannose, sodium chloride, a poly lactic acid, poly(lactic-co-glycolic acid), glycerol, a glycol, a surfactant, a plant gum such as xanthum gum, or a liposome.

The plant stem cell product may be encapsulated.

The plant stem cell product may be derived from a dedifferentiated cell from any plant species. In embodiments, the a dedifferentiated cell may be selected from a species in a group consisting of apple, lithy tree, mulberry, *cannabis*, hemp, mint, grape, *eucalyptus*, lingonberry, lungwort, oregano, plantain, poppy, elecampane, *lobelia*, orchid, osha root, garlic, ginger, turmeric, sage, mullein, licorice root, coltsfoot, thyme, adhatoda vasica, caraka samhita, albizzia *lebbeck*, boswellia *serrata, Curcuma longa, ocimum sanctum*, and *piper longum*.

The dedifferentiated cell may include a stem cell recovered from a part of a plant regenerating from an injury or the progeny of such a stem cell. The part of a plant may include one or more of a stem, a meristem, a leaf, a flower, a fruit, a seed, a root, or a callus.

In embodiments, the plant stem cell product may include an apple stem cell product. The apple stem cell product may comprise an extract of an apple stem cell, where the apple stem cell is derived from dedifferentiated cells recovered from an injured portion of an apple plant. The apple stem cell product may be encapsulated in a liposome comprising a phospholipid, glycerin, and xanthum gum. In some of these embodiments, the aerosolizing device includes an electronic-cigarette.

The plant stem cell stem cell may be from an *Asparagales* species or from a species that has in its telomeres the repeated 6-mer sequence TTAGGG. The telomere may include a plurality of contiguous copies of the TTAGGG sequence. The plant stem cell may be derived from a monocot *Asparagales* species. In other embodiments, the plant stem cell may have in its telomeres the repeated 12-mer sequence CTCGGTTATGGG.

In other embodiments, the invention includes a plant SC product applied in a divisible vehicle. A divisible vehicle is a composition that may be applied to a part of the body so that a plant SC product may treat directly the part of the body or may be transported by the body to a different part of the body to be treated. Transport by the body may include suspension, dissolution, or extraction in a body fluid such as blood, interstitial fluid, tears, saliva, phlegm, or mucous. Examples of divisible vehicles include creams, gels, polymers, lubricants, mixtures, emulsions, gums, or oils in which plant SC products may be suspended or dissolved. A plant SC product applied in a divisible vehicle may include any of the combinations described above with respect to embodiments that include a delivery device.

The aerosolizing device may include one or more of a nebulizer, a pressurized metered-dose inhaler, a personal vaporizer, a humidifier, a personal diffuser, a traditional cigarette, or an electronic-cigarette.

In embodiments, the invention includes a method of treating condition at a treatment site in a respiratory system of a mammal. The method includes steps of providing a plant stem cell product, aerosolizing the plant stem cell product, and delivering the aerosolized plant stem cell product for inhalation into the respiratory system. The aerosolized plant stem cell may be delivered at a flow rate and with a particle size distribution such that at least 30% of the plant stem cell reaches a targeted treatment site. In other embodiments, the invention includes a more general method of treating a portion of the body by providing a plant stem product and a delivery device configured to deliver the product to the portion of the body to be treated, and delivering the plant stem cell product to the portion to be treated using the delivery device. In some embodiments, the tissue may be an internal tissue only, that is, a tissue other than skin. Some skin treatments may benefit from an appropriate delivery device. For example, a condom treated with a plant SC product may serve to as a delivery device the plant SC product to either male or female genitals.

The targeted treatment site for the method may include one or more of a bronchus, a bronchiole, an alveolus, a lung parenchyma, or a capillary bed. The particle size distribution may include more than 50% of particles less than about 5 μm. In embodiments, the particle size distribution may include a range of about 0.5 μm to about 5 μm where the treatment site includes a bronchus or a bronchiole. The particle size distribution may include a range of about 100 nm to about 600 nm where the treatment site includes an alveolus, a lung parenchyma, or a capillary bed.

The plant stem cell product used in the method may include any of the combinations described above with respect to the system of the invention. The plant stem cell product may include one or more of a plant stem cell extract, a lyophilized plant stem cell, a plant stem cell culture medium, or an intact plant stem cell. The plant stem cell may also include a pharmacologically suitable excipient.

The treated lung condition may include one or more of a cancer, asthma, a lung inflammation, an infection, chronic obstructive pulmonary disease, emphysema, cystic fibrosis, and a lung irritation. The method may treat the lung condition through one or more of lung regeneration, a bronchodilatory effect, a tissue regeneration effect, a tumor suppression effect, a cancer cytotoxic effect, a clearing of free radicals, a cartilage regeneration effect, an anti-inflammatory effect, and a mucus reduction. In embodiments, the method treats a lung condition through one or more of an antioxidant effect, an anti-inflammatory effect, a regeneration effect, or a cytotoxic effect.

BRIEF DESCRIPTION OF THE DRAWINGS

FIG. 1 shows micrographs of selected results of scratch assays in lung epithelial cell cultures treated with an apple stem cell embodiment of the plant extracts of the invention.

FIG. 2 shows a graph of summary results of the scratch assays of FIG. 1.

FIG. 3A-3G show micrographs of scratch assays for cells treated with controls or embodiments of plant cell materials of the invention.

FIG. 4 is a summary graphical representation of control-ratioed scratch assay results exemplified in FIGS. 3A-G.

FIG. 5 shows a graph of TNF-α release inflammatory response from stimulated mouse macrophages when treated with an apple stem cell embodiment of the invention.

FIG. 6 shows a graph of cytotoxicity activity of an apple stem cell embodiment of the invention on lung tumor cell lines A549 and NCIH520 and on a lung epithelial cell line.

FIG. 7 shows fluorescence micrographs of acridine orange/ethidium bromide staining of A549 cells treated with an apple stem cell embodiment of the invention.

FIG. 8 shows fluorescence micrographs of acridine orange/ethidium bromide staining of NCI-H520 cells treated with an apple stem cell embodiment of the invention.

FIG. 9 shows fluorescence micrographs of Calcein AM staining in A549 Lung Cancer Cell Line cells treated with an apple stem cell embodiment of the invention.

FIG. 10 shows fluorescence micrographs of Calcein AM staining in NCI-H520 Lung Cancer Cell Line cells treated with an apple stem cell embodiment of the plant stem cell of the invention.

FIG. 11 shows a graph of cytotoxicity activity of an apple stem cell embodiment of the invention on lung tumor cell lines A549 as measured by lactate dehydrogenase release.

FIG. 12 shows a graph of cytotoxicity activity of an apple stem cell embodiment of the invention on lung tumor cell line NCIH520 and on a lung epithelial cell line as measured by lactate dehydrogenase release.

FIG. 13 shows a graph of reduction of oxidation produced by an apple stem cell embodiment of the invention.

DETAILED DESCRIPTION

I have discovered that plant stem cells beneficially affect human (or other mammalian) tissues and cells. Exposure may be to plant stem cells or to their products, contents, or enriched media (collectively "plant SC products"). As used herein, enriched media refers to culture materials in which plant stem cells are grown and that is subsequently harvested. Such enriched media contains stem cell products, contents, and by-products of plant stem cell growth.

Human tissues are subject to injury from defects, diseases, insults, injury, trauma, or conditions including one or more of oxidative damage, inflammation, wounds, or cancer. The plant stem cell products of my invention may treat such injuries by a combination of effects, including antioxidant effects, anti-inflammatory effect, regeneration effects, or cytotoxic effects.

Oxidative damage can arise from normal metabolism, including aerobic respiration such as mitochondrial electron transport. Oxidative damage may also arise in response to infectious organisms or immune system action. Oxidative damage may also arise from therapeutic interventions, including radiation therapy. While cells and tissues possess endogenous protective agents against oxidative damage, these agents may be depleted. In some circumstances the endogenous protective agents, which include reservoirs of small molecule antioxidants as well as inducible antioxidant enzymes, may not be adequate to completely prevent oxidative injury. Notably, these endogenous protective agents diminish with age. I have found in a model system that plant SC products have antioxidant activities that may prevent or reduce oxidative damage to affected cells when applied to the cells.

Inflammation is a response of the body to infection, irritation, or tissue damage. Inflammation marshals the body's defenses to effectively respond to these conditions. In some circumstances, secondary effects of inflammation produce additional harm. In other circumstances, inflammatory reactions may arise in inappropriate situations, such as in autoimmune diseases.

Inflammation is mediated by cellular communication, which may be through cell-to-cell contact or through the release of soluble cytokines. These cytokines contribute to modulation of the response, to recruitment of additional cells to the inflammatory process, and to targeted attack against organisms or tissues recognized as foreign. Many cytokines are intimately associated with some of the undesirable effects of inflammation. For example, Tumor necrosis factor alpha (TNF-α) is a cell signaling protein (cytokine) involved in systemic inflammation and is one of the cytokines that make up the acute phase reaction. Specifically-targeted injectables, such as humanized monoclonal antibodies with specificity to TNF-α (e.g. adalimumab), can ameliorate some of the undesirable effects of inflammation in autoimmune conditions.

I have found that plant SC products can act upon activated inflammatory cells in a model system to reduce the release of inflammatory cytokines, including TNF-α. The plant SC products may thus have a beneficial effect on inappropriate inflammatory activity when applied to the activated cells. The plant SC products, because they prevent release of cytokines, may have a synergistic effect to agents such as adalimumab because of the different mechanisms of action, i.e. preventing TNF-α release as opposed to inactivating already-released TNF-α.

Wound healing is a beneficial response to insult or injury where cells adjacent to the site of an injury or recruited to the site of an injury respond by closing wounds and repairing or replacing damaged tissue.

I have found that plant SC products can encourage tissue regeneration and wound healing in a model system. The plant SC products may have a beneficial effect on the regeneration of tissues following trauma or injury when applied to the injured tissue.

Cancer is an abnormal replication and infiltration of cells that have escaped regulatory control. It may be caused by accumulation of mutations at many loci to produce a large variety of phenotypes. Recently developed drugs targeted to specific pathways have been effective against many forms of cancer, but the continuing accumulation of mutations frequently allows some tumor cells to escape this specific therapy.

The fallback treatment in many cases remains cytotoxic agents that kill tumor cells less discriminately. Such cytotoxic agents are valuable if they are more lethal to cancer cells than to the exposed normal cells. A therapeutic ratio of greater than one indicates that a treatment kills cancer cells more readily than noncancer cells. I have found that plant SC products, when applied to cells of a model system, can be more than ten times more effective at killing cancer cells than normal cells. The plant SC products may have a beneficial effect if brought into contact with cancer cells.

Somewhat paradoxically, plant SC products may protect cells from oxidative damage, promote regeneration, and may have a cytotoxic effect. The net effects may depend on access to the treated cells, the inflammatory and oxidative environments, the treatment concentrations and exposure times, or other factors.

Lung conditions may benefit from direct application of plant SC products to lung tissues. I have found that a suitable method for providing exposure to plant SC products is aerosol delivery of plant SC products to a treatment site in the respiratory system of a mammal.

Plant stem cells, such as apple stem cells, may stimulate human stem cells, protect against reactive oxygen species or uv-induced cell death, mitigate aging related alterations in gene expressions, and reverse or block telomere shortening.

Other plant stem cells such as those from lithy tree, mulberry, *cannabis*, hemp, mint, grape, *eucalyptus*, lingonberry, lungwort, oregano, plantain, poppy, elecampane, *lobelia*, chaparral (larrea tridentate), orchid, osha root, garlic, ginger, turmeric, sage, mullein, licorice root, coltsfoot, thyme, adhatoda vasica, caraka samhita, albizzia *lebbeck*, boswellia *serrata, Curcuma longa, ocimum* sanctum, or *piper longum* may have similar or other beneficial effects. In some cases, a particular plant stem cell may not be suitable for some applications. For example, U.S. Pat. No. 8,617,621B2 to Lim et al. described feeding of a dried *ginseng* stem cell preparation to mice that increased the activity of mice NK cells. This is contrary to the observed anti-inflammatory effects of my preparation. Thus, stem cell products derived from *ginseng* stem cells may not be suitable for all applications. In other cases, plant stem cell extracts may have an anti-inflammatory effect but may not support other effects. For example, KR101212032B1 to Lee et al. describe *chrysanthemum*-derived stem cells as having an anti-inflammatory effect on a mouse macrophage cell line. No other effects were described; stem cell products derived from *chrysanthemum* may not be suitable for all applications. In still other cases, a plant stem cell may be from a plant that is known to produce medications effective against certain cancers. For example, U.S. Pat. No. 8,790,927 B2 to Park, et al. described an anticancer effect in mice from ingestion of a cell line derived from a *Taxus* (yew) cambium. *Taxus* species are the original source of the chemotherapeutic drug paclitaxel. While Park asserted that the cell line tested negative for paclitaxel, he also reported that when the cell line was cultured in a medium containing an elicitor, it can produce paclitaxel at a high concentration. It is thus possible that the cell line owes its anticancer effects to the production of the known drug paclitaxel. Because this would be an effect of the drug rather than an effect of the plant stem cell product itself, *Taxus*-derived plant stem cell products may not be suitable for all applications. It is expressly within the scope of my invention to exclude certain stem cell types. In some embodiments, the systems and methods of my invention may be limited to plant stem cell products other than *ginseng* or *Taxus* stem cells.

Without intent to be bound by theory, Applicants believe that certain plant stem cells, because they share at least some signal motifs with other eukaryotes including humans, can produce beneficial modulation of human signaling pathways. For example, *Arabidopsis*-type 7-mer stem cell telomerase may act on the repetitive human 6-mer telomere sequence TTAGGG. *Asparagales* type 6-mer stem cell telomerase may also act on the human telomere with its identical sequence specificity. The long evolutionary distance between human and plant telomerase enzymes suggests that the plant enzymes may act in different circumstances and under different conditions than the human enzyme. This likely different action may fortuitously remedy defects in human metabolism and cell proliferation, particularly when defects are related to cell proliferation or cellular senescence.

There may be other as yet unidentified convergences in plant and human signaling pathways that present further opportunities for therapeutic effects.

Further, since plant stem cells include genes and pathways that may produce biologically active compounds, these cells may be capable of delivering such active compounds to treat human disease.

As discussed above with respect to *Ephedra*, systemic application of plant products may cause unwanted effects. Further, some plant cell compounds may not be well absorbed systemically as discussed above for unconjugated quercetin. Most macromolecules cannot be administered orally because proteins are digested before they are absorbed into the bloodstream. Also, their large size prevents them from naturally passing through the skin or nasal membrane, and therefore they may not be administered transdermally without the use of penetration enhancers.

There remain a range of administration methods that can bring plant SC products into contact with tissue to be treated. These include ingestion in protected form, injection, transluminal arterial or venous delivery, topical application to mucous membranes of the mouth, nose, eyes, oropharynx, genitals, or digestive tract, or topical application to skin with penetration enhancers. These administrative routes involve specialized delivery devices.

In embodiments, the invention includes a plant SC product and a delivery device configured to deliver the plant SC product to a particular location of the body. This beneficially supports localized treatment to avoid untargeted effects. The delivery device may be any of an aerosolizing device, an injection device, a topical applicator, an eyedrop applicator, an eardrop applicator, a condom, a buccal applicator, a rectal or vaginal suppository, an ingestible capsule, a catheter, or another device with a similar ability to deliver an aliquot of plant SC products to a targeted treatment site. In some embodiments, the tissue may be an internal tissue, that is, a tissue other than skin, because most parts of the skin may be directly accessible without a delivery device.

An injection device may comprise a syringe and hollow needle sized for subcutaneous injection, for intradermal injection, for intramuscular injection, for intravenous injection, for intracapsular injection, intraarticular injection, for intraosseous injection, for intraperitoneal injection, for intracavernous injection, or for cardiac injection. These devices are well-known in the art and will not be further described.

Catheters may be used as delivery devices to deliver plant SC products to the gastrointestinal system or to the urethra or bladder. Angio-catheters may be used as delivery devices to deliver plant SC products to any of a large number of selected locations in the vasculature. For example, a catheter inserted transluminally into the femoral or the brachial artery can reach most major blood vessels to deliver plant SC products to the vasculature of an organ or a localized segment of tissue. These devices are well-known in the art and will not be further described. In other embodiments, a suppository containing a plant SC product may be inserted into the rectum or vagina to treat tissue there. An ingestible capsule containing a plant SC product may be swallowed to treat portions of the digestive tract or to treat the body systemically.

Topical applicators exist in a variety of forms such as cotton or foam-tipped swabs, adhesive patches, wound dressings, pipettes, and bandages. When skin is injured and the treatment is of the injury directly, the topical applicator may be directly applied to the injured skin. As noted above, in some embodiments, the tissue may be an internal tissue only, that is, a tissue other than skin. Some skin treatments may benefit from an appropriate delivery device. For example, a condom treated with a plant SC product may serve to apply the plant SC product to either male or female genitals. The plant SC product may be mixed with a lubricant applied to a condom.

When used to apply plant SC products to uninjured skin, a topical applicator may incorporate permeation enhancers. Permeation enhancers may reversibly compromise the skin's barrier function and allow the entry of otherwise poorly penetrating materials. Permeation enhancers include materials such as fatty acids, terpenes, fatty alcohol, pyrrolidone, sulfoxides, laurocapram, surface active agents, amides, amines, lecithin, polyols, quaternary ammonium compounds, silicones, or alkanoates.

In some embodiments, the skin's barrier function may be degraded mechanically by delivery devices that abrade surface skin (dermabrasion) or pricking with sharp applicators such as microneedle arrays. In other embodiments the skin's barrier function may be degraded electrically by applying an electroporation voltage to the treated region.

Plant SC products in the form of eyedrops may be administered to the sclera of the eye using a pipette as the delivery device. Similarly, plant SC products in the form of eardrops may be administered into the ear canal.

An aerosolizing device delivers finely divided portions such as droplets for inhalation. Aerosols containing plant SC products may be produced by a variety of devices including sonic nebulizers, e-cigarettes, vaporizers, powder or liquid droplet inhalers, humidifiers, or nasal sprays. The size of aerosol droplets, their concentration, and airflow velocity profile determine the distribution of product delivery in the lung.

In other embodiments, the invention includes a plant SC product applied in a divisible vehicle. A divisible vehicle is a composition that may be applied to a part of the body so that a plant SC product may treat directly the part of the body or may be transported by the body to a different part of the body to be treated. Transport by the body may include suspension, dissolution, or extraction in a body fluid such as blood, interstitial fluid, tears, saliva, phlegm, or mucous. Examples of divisible vehicles include creams, gels, polymers, lubricants, mixtures, emulsions, gums, or oils in which plant SC products may be suspended or dissolved. A plant SC product applied in a divisible vehicle may include any of the combinations described in this application with respect to embodiments that include a delivery device.

A divisible vehicle such as a cream, lotion, gel, or emulsion containing a plant SC product may be applied to the skin, to mucosa, to the scalp, or to a wound. A polymer mixture such a chewing gum containing a plant SC product may be used to expose the buccal mucosa to the plant SC product for an extended period. Saliva developed while chewing the gum may transport the plant SC products to the buccal mucosa. A mixture such as a mouthwash containing a plant SC product may be applied to the oral cavity for an extended period, thereby treating portions of the oral mucosa. A surfactant or conditioner mixture such as a shampoo or conditioner containing a plant SC product may be applied to treat the hair or scalp. A lubricant mixture containing a plant SC product may used during coitus to deliver the plant SC product to the genitals.

In some embodiments, the plant SC products include an excipient. Suitable excipients include one or more of lactose, mannose, sodium chloride, poly lactic acid, poly (lactic-co-glycolic acid), glycerol, glycol, a surfactant, or a liposome. The excipient may serve to buffer the plant SC products or to adjust its viscosity or heat capacity to tune the aerosol generation process. Excipients may also adjust hydrophilicity of the materials to control aerosol particle size.

Plant SC products may be treated by encapsulation to help enhance stability by protecting the plant SC products from exposure to environmental materials or conditions that may degrade the activity of the active materials. Encapsulation may also serve to control the release of active materials to a desired time (e.g. when exposed to the lung surface) or at a desired rate. Encapsulation may be performed by any method known in the art, including those reviewed by Yadav et al. in Peptides 32 pp. 173-187 (2011). This review is hereby incorporated by reference for its disclosure of methods of encapsulation. Any of these encapsulation methods may be used with any of the delivery devices for any appropriate treatment site.

In some embodiments, a suitable method of encapsulation includes emulsification polymerization using aqueous phase methacrylate monomer and a photoinitator such as benzoin ethyl ether emulsified with plant SC products with polyethylene oxide as a stabilizer and exposure to UV light after emulsification to produce poly(methacrylate) encapsulated active components of plant SC products. The capsules may range from about 50 to about 5000 nm in diameter. While the capsules may be close to monodisperse (depending on the method of preparation), in some embodiments, the size of capsules may be deliberately widely distributed to control the rate of release of active materials. Widely distributed populations of capsules may be prepared by altering the conditions of emulsification during encapsulation or by mixing two or more batches of capsules with different size.

When intact plant stem cells are used, any capsules must be as large or larger than the size of the cells. When plant stem cell contents are extracted or removed from the intact cells then the capsule size is no longer limited by the cellular size. Such capsules may be selected primarily based upon the targeted region of the lung or upon sizes that may be more compatible with aerosolization processes. For example, if plant stem cell contents are removed by lysis, homogenization, or ultrasonic disruption, or when plant SC products include an enriched medium that is subsequently harvested (and optionally further purified or concentrated), these removed contents may be encapsulated.

In other embodiments, encapsulated plant SC products may be prepared as phospholipid nano-emulsions or as nano-liposomes.

Capsules containing plant SC products may be washed by dialysis, by centrifugal filtration, by tangential flow filtration, by centrifugation and decanting, or by other techniques known in the art, to produce washed encapsulated plant SC products. Washing helps remove unreacted monomers or initiator as well as materials not incorporated in capsules. Alternatively, and depending on the materials used in the encapsulation process, encapsulated plant SC products may be used without further processing. After washing, encapsulated plant SC products may be resuspended in a buffer, in sterile saline, in water, or in a suspension containing other excipient materials. In some embodiments, the resuspension material may have viscosity, heat capacity, or hydrophilicity selected to optimize aerosolization of the plant SC products.

The location of deposition of aerosolized particles depends on aerosol size distribution, sometimes expressed as mass median aerodynamic diameter (M MAD). Fine aerosols are distributed in peripheral airways but deposit less material per unit surface area than larger particle aerosols because their volume is lower. Larger particle aerosols deposit more drug per unit surface area, but this is preferentially targeted to larger airways. The precise location of deposition depends on airway caliber and structure, which differ between individuals. In general, large conducting airways and oropharyngeal region receive aerosols with a MMAD of 5-10 µm. Smaller particles (1-5 µm in diameter) deposit in small airways and alveoli. More than half of 3 µm particles deposit in the alveolar region.

Individual pathology differences can also affect aerosol deposition. For example, the airway narrowing in mild to moderate asthma is more responsive to 2.8 µm aerosols than to either 1.5 µm or 5 µm aerosols. This is likely due to a combination of penetration depth and distribution of affected tissue since smooth muscle (the tissue that produces airway narrowing) is not present in the alveolar region.

The size of particles in the lung is not necessarily the same as when introduced because the lung has a relative humidity of about 99.5%. A hygroscopic aerosol delivered at relatively low temperature and humidity into one of high humidity and temperature would increase in size during inhalation. This effect is more important for smaller particles because of their higher surface area relative to volume. Suitable excipients such as salts or sugars may control water absorption for a more predictable aerosol size distribution.

Particles not deposited during inhalation are exhaled and thus lost. Deposition due to sedimentation affects particles down to 0.5 µm in diameter, whereas below 0.5 µm, the main mechanism for deposition is by diffusion.

The distribution of deposition of aerosolized particles also depends on the position of the patient. For example, in experiments with 4 micrometer aerosols, NR Labris and MB Dolovich in *Br J Clin Pharmacol*, 56, 588-599 reported a 2:1 ratio between lower and upper lobes when the treated person was upright. This gradient is reduced when the patient is supine.

Inhalable aerosols may be produced in a variety of methods including swirl nozzles, venturi atomizers, T-jets, vibrating-mesh nebulizers, heated wicks, vibrating nozzles, and electrospray systems, among others. Most involve the interaction of a gas stream (usually air) and a liquid flow to break up the liquid into discrete particles separated by the flowing air. Suitable methods for delivering the plant SC products may be categorized by the source of the gas stream and by how the liquid flow is broken up.

For inhaled aerosols, the gas stream may be produced by a pump or stored gas or by breathing. Pump or stored gas-based methods advantageously offer repeatable flow rates and pressures and can reduce the work a user need perform to inhale an aerosol. This reduction of work may be of consequence when the treated patient has reduced lung function that may be a consequence of the treated condition.

In some embodiments, the invention delivers the plant SC products using a nebulizer or a pressurized metered-dose inhaler. Nebulizers and pressurized metered-dose inhalers use pumps and stored gas to advantageously produce aerosols that may be less dependent on user technique.

Nebulizers are common medical devices that use air pumps to produce (or help propel) aerosols for therapy. These convert liquids or suspensions into aerosols with a particle size that can be inhaled into the lower respiratory tract. There are pneumatic jet nebulizers, ultrasonic nebulizers, and mesh nebulizers. Some nebulizer designs may be breath-enhanced or breath-actuated. These devices are well-known in the art and will not be further described.

Medical nebulizers advantageously permit adjustment of flow rates and (indirectly) aerosol size distribution. This permits more accurate targeting of delivery of plant SC products to the desired treatment location.

The pressurized metered-dose inhaler is a commonly-used device that uses stored gas under pressure for aerosol production and delivery. There are press-and-breathe and breath-actuated pressurized inhaler designs. These devices are well-known in the art and will not be further described.

Pressurized metered-dose inhalers advantageously are portable and easily operated. These devices typically are designed for use with relatively high concentration medications (such as albuterol for asthma) so that aerosol volume per actuation is usually small. In some embodiments, the invention includes use of pressurized metered-dose inhaler loaded with plant SC products and an inert drive gas. In such embodiments, the plant SC products may be concentrated to provide an effective dose in one or a few operations.

In other embodiments, the invention delivers plant SC products using a device where the gas stream is produced by breathing. Such systems advantageously allow for aerosol delivery over an extended period of time without interfering significantly with other life activities. This may especially valuable when treatment aerosols comprise fairly low concentration materials. Many plant SC product treatment compositions may be of fairly low concentration.

Breathing-based aerosol delivery devices include powder inhalers, traditional cigarettes, personal vaporizers, also known as personal diffusers, electronic cigarettes, or e-cigarettes. Powder inhalers, such as commercial Spinhaler and Twisthaler devices, deliver a dose of a powder during inhalation. Such devices may be used in embodiments of the invention by drying the plant SC products to produce a finely divided powder. Traditional cigarettes combust materials to produce a smoke that may contain uncombusted components. These may be used in embodiments of the invention by applying the plant SC products to a combustible material such as paper or leaves. Some personal vaporizers use heat to produce an inhalable aerosol from a liquid or suspension drawn into a wick by capillary action. Users inhale these aerosols and can control puff pressure, puff length, and interval between puffs. With some devices, current applied to the heater may be adjusted. Other personal vaporizers, such as personal diffusers, may use heat to directly produce a vapor that may then be inhaled.

Typical aerosols from personal vaporizers have particle diameters in the 250-450 nm range and particle density concentration of approximately $10^9$ particles/cm$^3$. These relatively small aerosol particles should target a user's entire lung, including the alveolar region. Because they may be used for extended period, a user may alter posture between upright and supine to better distribute the aerosols to a targeted region.

In other designs, piezo-electric, ferroelectric, or magnetostrictive vibrators may produce the aerosol. Use of personal vaporizers including vibration to produce aerosols may advantageously produce an unheated aerosol that may be adjusted for particles in the micrometer range. This may be particularly appropriate for plant SC products that include intact cells.

Although the variations in user operation parameters such as puff pressure can affect the rate of plant SC product delivery, use of personal vaporizers can compensate for these variations by loading a predispensed dose of plant SC product into the personal vaporizer. The device may then be used until the preloaded dose is exhausted. This may be especially advantageous where extended treatment times are desired, as may be the case with plant SC products.

Personal vaporizers may be designed (or adjusted) to produce a controlled aerosol particle size by adjusting the size of the capillary openings in the heated wick, by adjusting the current to the heater, or by adjusting the viscosity and heat capacity of excipients mixed with the plant SC materials. The inventive method may include such adjustments to control the aerosol size distribution. In embodiments, the size may be adjusted to produce aerosols having a size distribution in the range of about 100 nm to about 600 nm where the treatment site includes an alveolus, a lung parenchyma, or a capillary bed. Where the treatment site includes a bronchus or a bronchiole, the particle size distribution may be adjusted to include particles in a range of about 0.5 µm to about 5 µm.

Many personal vaporizers include breath sensors that may permit adjustment of heater current during inhalation. In some embodiments, the invention includes tuning of heater current to produce a desired aerosol size distribution. This may include individual adjustment based upon breath sensor measurement.

The examples below describe a collection of experiments designed to demonstrate the effectiveness of plant stem cell products in model systems comprising cultured cell lines including human lung cell lines and mouse macrophage cell lines. Scratch assays used a normal human epithelial line to ascertain the effect of plant stems on cell regeneration. A cytokine release assay evaluated anti-inflammatory activity using an activated mouse macrophage cell line. Two human lung cancer cell lines (a lung adenocarcinoma and a squamous carcinoma) were compared to a normal lung epithelial cell line to determine treatment efficacy and cancer-specific cytotoxicity.

Apple stem cell extracts were tested in each of the assay types. Other plant stem cells, as well as other plant extracts, were evaluated in scratch assays using the normal human epithelial line and in cytoxicity assays comparing effects on the human lung adenocarcinoma cell line and the normal human epithelial cell line.

The purpose of testing plant extracts other than plant SC products was to provide a comparison. Plant extracts other than plant SC products would be expected to have some effects in some cases. Such extracts are the source of many types of effective drugs, so some effects are reasonably expected.

Example 1: Plant Stem Cell Extracts

The following plant stem cell extracts were tested for biological effects. Plant stem cells refer to dedifferentiated replicating cells isolated from a part of a plant regenerating from an injury and their progeny. Injury sites may be from any portion of a plant such as callus, leaves, fruit, stems, flowers, roots, meristem, root cap, or seeds. Other plant stem cells may be derived from cells of a developing plant embryo, from a plant callus, or from plant tissue samples (explants) in tissue culture medium in vitro. Plants stem cells may be derived from many different cell types and may be able to differentiate into a whole plant.

Apple stem cell culture extract (ASC) was purchased from Lotioncrafter LLC of Eastsound, Wash. This composition included a lysate of dedifferentiated cells from *Malus domestica* callus. The cells were derived from Swiss apple variety Uttwiler Spatlauber. The extract was prepared by encapsulating a lysate of cultured cells in liposomes composed of soy phospholipids (0.14% weight/volume ("w/v")), glycerin (0.4% w/v), and xanthan gum (1% w/v). The liposomes were suspended in about a 10% suspension in deionized water adjusted to pH 7.4 with 1.4% w/v phenoxyethanol as a preservative.

Lingonberry Stem Cell (LSC) extract was purchased from MakingCosmetics.com Inc. of Snoqaulmie, Wash. This composition included water, glycerin, *Vaccinium Vitis Idaea* fruit extract, xanthun gum, sodium benzoate, gluconolactone, and calcium gluconate. *Vaccinium Vitis Idaea* is a short evergreen shrub in the heath family that bears edible fruit, native to boreal forest and Arctic tundra throughout the Northern Hemisphere from Eurasia to North America.

Orchid Stem Cells (OSC) extract was purchased from MakingCosmetics.com Inc. of Snoqaulmie, Wash. This composition included water, glycerin, Calanthe discolor extract, xanthun gum, sodium benzoate, gluconolactone, calcium gluconate. Calanthe discolor is a species of orchid native to eastern Asia.

Example 2: Plant Extracts

The following plant extracts other than plant stem cell extracts were tested for comparison with plant stem cell extracts.

Apple Fiber Powder (AFP) was purchased from Starwest Botanicals of Sacramento, Calif. This composition included powder from *Pyrus Malus*. *Pyrus Malus* is a former taxonomic grouping applied to the apples, pears and related plants of the subfamily Maloideae.

Dandelion Root Extract (DRE) was purchased from Starwest Botanicals of Sacramento, Calif. This composition included *Taraxcum officinale* root extract, water, and alcohol (30%). *Taraxcum officinale* is a flowering herbaceous perennial plant of the family Asteraceae (Compositae). It can be found growing in temperate regions of the world.

Aloe Vera Juice (AVJ) was purchased from Starwest Botanicals of Sacramento, Calif. This composition included decolorized *Aloe barbedensis*, citric acid and sodium benzoate. *Aloe barbedensis* is a succulent plant species of the genus *Aloe*. An evergreen perennial, it originates from the Arabian Peninsula but grows wild in tropical climates around the world and is cultivated for agricultural and medicinal uses.

*Ginkgo* Leaf Extract (GLE) extract was purchased from Starwest Botanicals of Sacramento, Calif. This composition included *Ginkgo biloba* Leaf extract, water and alcohol (30%). *Ginkgo biloba* is a large tree native to China; the tree is widely cultivated.

Example 3: Target Cells

Human lung adenocarcinoma cell line A549, human squamous carcinoma cells line NCI-H520, and "normal" lung epithelial cell line L132 were procured from National Centre for Cell Sciences (NCCS), Pune, India. RAW 264.7 mouse macrophage cell lines were used for inflammation assays.

Example 4: Scratch Gap Regeneration Assay I

Scratch assay determines effects of a treatment on cell migration and proliferation. In a typical scratch assay, a "scratch or wound gap" is created in monolayer cell culture by scratching and creating a gap in the culture. "Healing" of the gap by growth and cell migration towards the center of the gap is monitored and measured. Various factors that alter the migration and growth of the cells to bridge the gap can lead to increased or decreased "healing" rate of the gap. Scratch assay on normal lung cell line L132 was performed to evaluate regenerative potential of the apple stem cell extract.

Method: Human lung epithelial cell line L132 cells were cultured in Dulbecco Modified Eagle Medium with 10% fetal bovine serum (FBS). Cells were seeded (0.05×10$^6$) into 24-well tissue culture plate. At about 80% confluence, a scratch in a straight line was created across the center of the well with a sterile 1 ml pipette tip. The long axial of the tip was held perpendicular to the bottom of the well to create a uniform scratch. Wells were washed after the scratch and then supplemented with fresh culture media. Test wells were subjected to the media with the test material at one of 100 and 250 µg per mL of media. Media without added test materials served as a control. Cells were then cultured for another 24 hours, washed twice with PBS and then fixed with 3.7% Paraformaldehyde for 30 minutes. Pictures of the monolayer were taken on a microscope and the gaps were quantitatively evaluated using Image) software from (http://rsb.info.nih.gov/ij/download.html). All studies were performed in triplicate. Results of triplicate data points appear in the table below. Concentrations of ASC refer to a mass per volume of the lysate.

TABLE 1

Results of ASC scratch assay as analyzed by ImageJ software. Values are determined widths of scratched areas.

| ASC Scratch Assay | replicate 1 | replicate 2 | replicate 3 | Average | SD | SE |
|---|---|---|---|---|---|---|
| | initial gap width (mm) | | | | | |
| Control | 27.32 | 28.90 | 25.55 | 27.26 | 1.68 | 0.97 |
| 100 µg/mL | 24.43 | 25.55 | 26.65 | 25.54 | 1.11 | 0.64 |
| 250 µg/mL | 24.42 | 25.55 | 25.55 | 25.17 | 0.65 | 0.38 |

| ASC Scratch Assay | replicate 1 | replicate 2 final gap width (mm) | replicate 3 | Average | SD | SE |
|---|---|---|---|---|---|---|
| Control | 21.21 | 20.23 | 20.21 | 20.55 | 0.57 | 0.33 |
| 100 µg/mL | 12.21 | 13.32 | 13.33 | 12.95 | 0.64 | 0.37 |
| 250 µg/mL | 10.21 | 11.12 | 10.90 | 10.74 | 0.47 | 0.27 |

FIG. 1 shows the physical appearance of scratches in selected wells for this ASC scratch assay. The parallel lines disposed roughly vertically in each image are the boundaries of the scratch as determined by the ImageJ software.

| difference in width: 0-24 hours | replicate 1 | replicate 2 | replicate 3 | mean | standard deviation |
|---|---|---|---|---|---|
| Control | 6.11 | 8.67 | 5.34 | 6.71 | 1.42 |
| 100 µg/ml | 12.22 | 12.23 | 13.32 | 12.59 | 0.52 |
| 250 µg/ml | 14.21 | 14.43 | 14.65 | 14.43 | 0.18 |
| Ratio/control | | | | | |
| 100 µg/ml | 2.00 | 1.41 | 2.49 | 1.88 | 0.22 |
| 250 µg/ml | 2.33 | 1.66 | 2.74 | 2.15 | 0.21 |

Table 2 shows results calculated from the data of from Table 1 where each value was calculated as the difference in gap width between time zero and 24 hours, with replicates compared individually to remove gap width influence on results.

| Ratio/control | mean | standard deviation |
|---|---|---|
| 100 µg/ml | 1.88 | 0.22 |
| 250 µg/ml | 2.15 | 0.21 |

Table 3 shows results calculated from the data of from Table 1 where each value was calculated by forming a ratio of the mean difference of Table 2 to the mean difference of the control wells. Standard deviations were calculated by error propagation assuming errors were uncorrelated. These summary results showed a higher degree of scratch closure for the treated wells, with a higher degree of closure at the higher ASC concentration.

Figure 2:
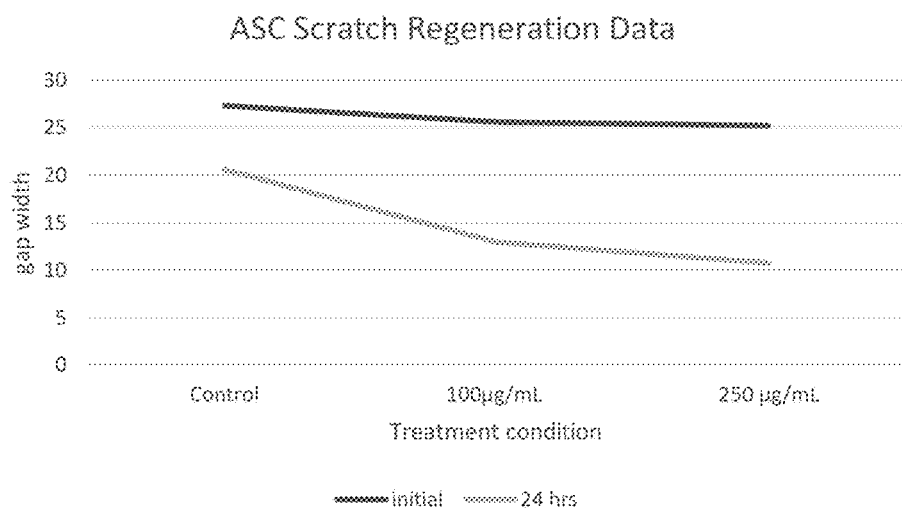

FIG. 2 is a graphical representation of these ASC scratch assay results. This shows a clear acceleration in closure of the gap in the treatment group as compared to untreated controls. The apple stem cell extracts produced faster regeneration of the cells in the gap at both the concentrations used after 24 hours treatment. The rate of gap closure was treatment dose dependent. Results were statistically significant at $p \leq 0.05$, indicating that apple stem cell extract can exert a positive effect in wound closing and regeneration of lung tissue.

Example 5: Scratch Gap Regeneration Assay II

The experiment of Example 4 was repeated, substituting other plant materials for ASC. Plant stem cell materials included Apple Fiber Powder (AFP), Dandelion Root Extract (DRE), *Aloe Vera* Juice (AVJ), *Ginkgo* Leaf Extract (GLE), Lingonberry Stem Cells (LSC), Orchid Stem Cells (OSC) as described in Examples 1 and 2. Example 5 experiments were performed with a common set of control wells. Concentrations of each material refer to mass of each as-supplied material. Each material was first prepared as a 1000 μg/mL stock in in Dulbecco Modified Eagle Medium with 10% FBS.

Figure 3A:
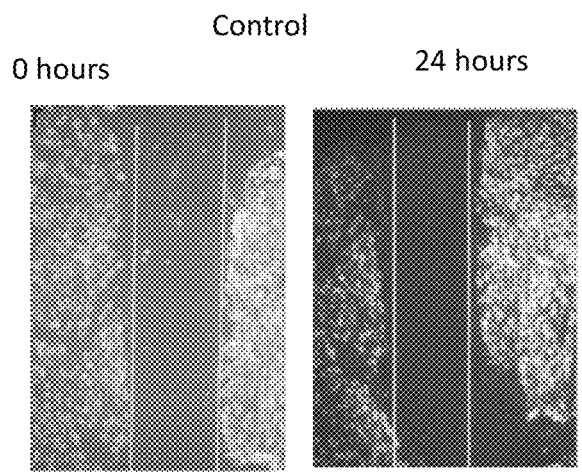
Figure 3B:
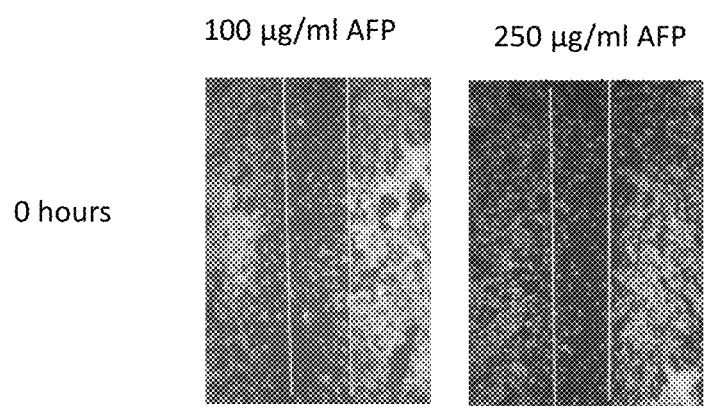
Figure 3B:
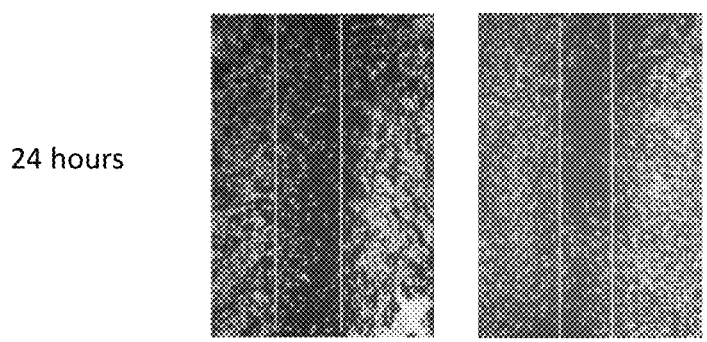
Figure 3C:
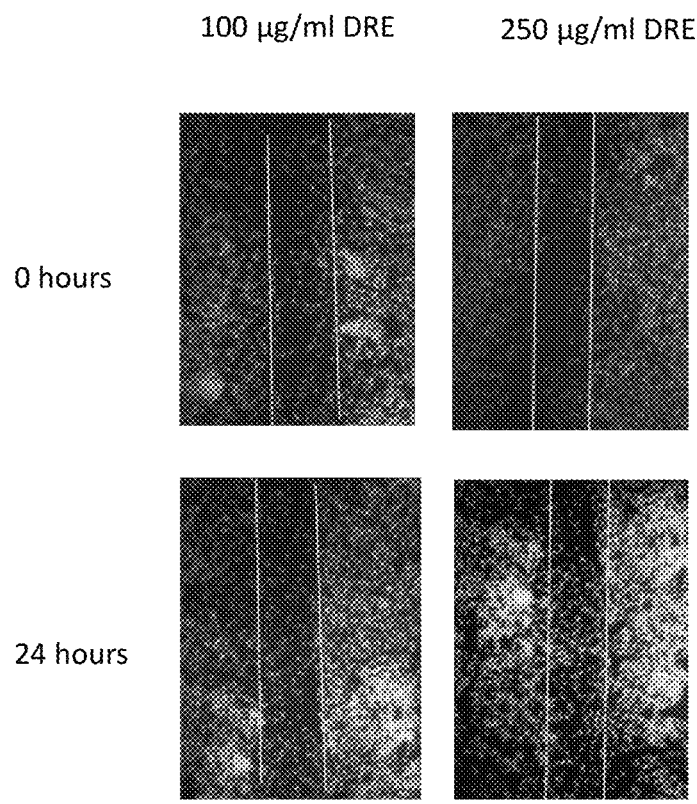
Figure 3D:
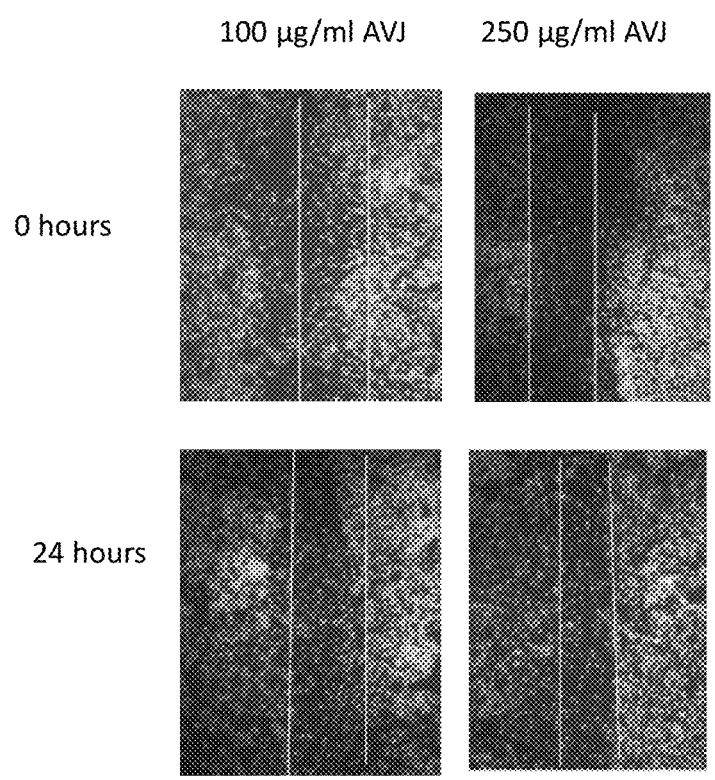
Figure 3E:
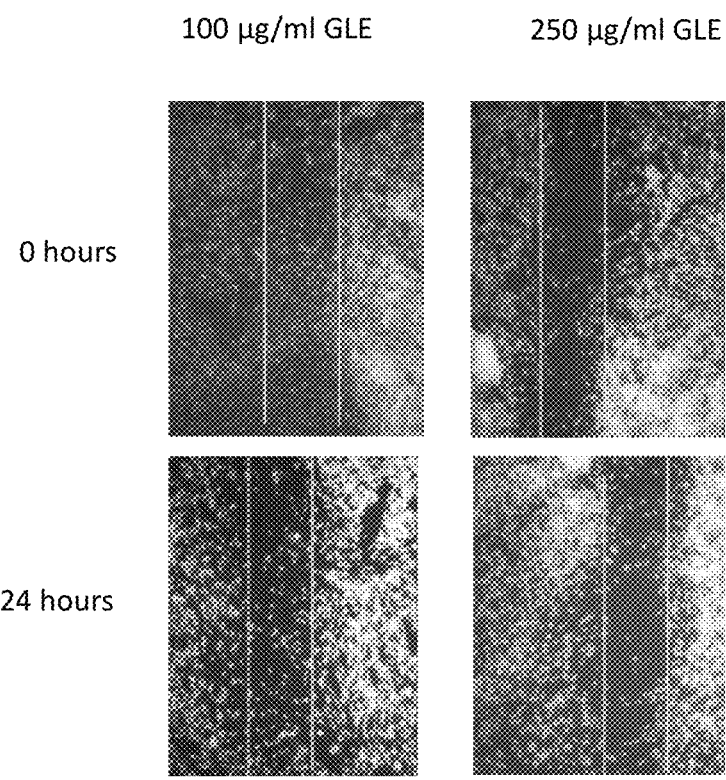
Figure 3F:
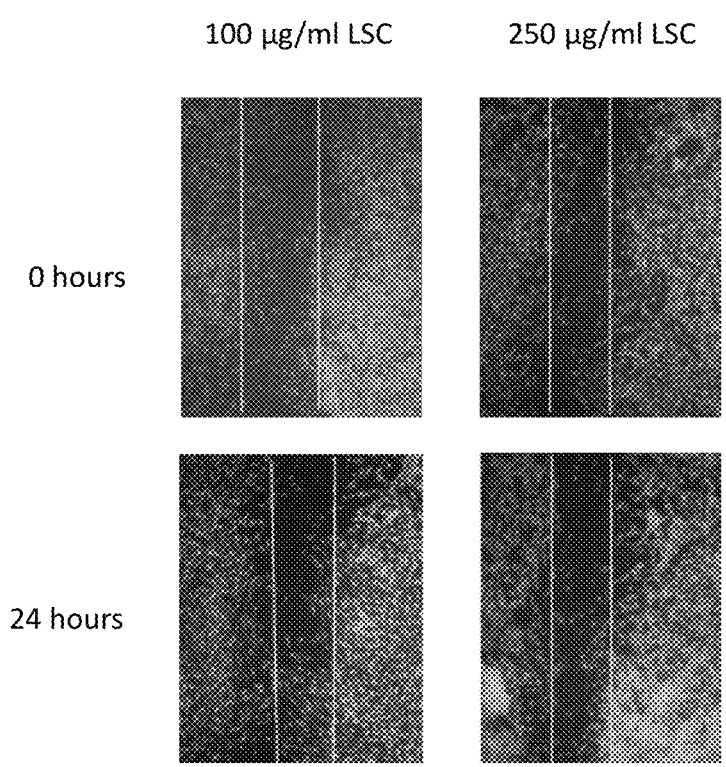
Figure 3G:
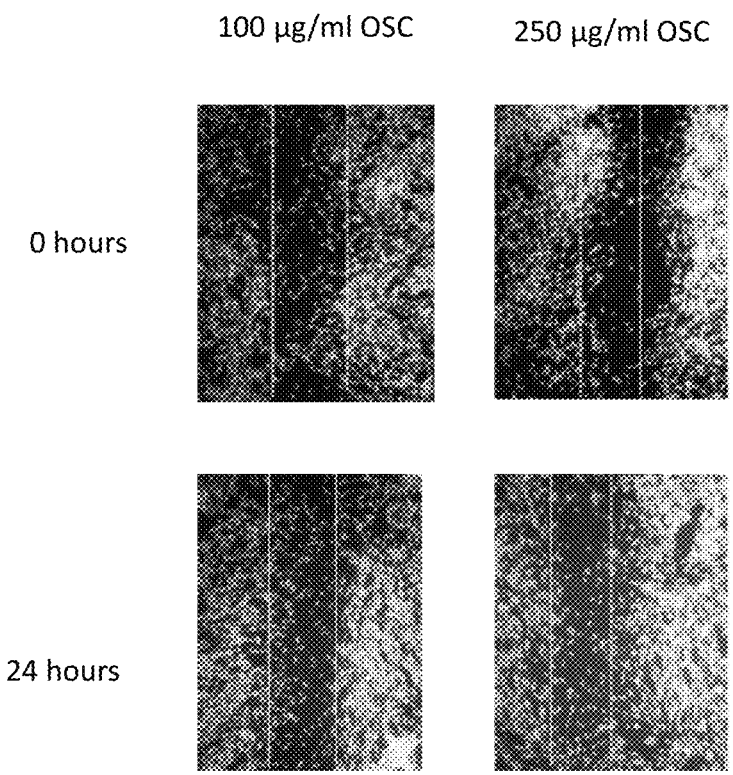

FIGS. 3A-3G shows monochrome images of phase contrast micrographs of selected wells of control and treated cells at the start of the experiment and 24 hours later (fixed with paraformaldehyde). The lines running roughly parallel to one another in each micrograph are the boundaries of the scratched region as determined by the ImageJ software. FIG. 3A shows control-treated wells. FIGS. 3B through 3G show one well for each treatment at each concentration at the start of the experiment and the same well 24 hours later. Note the increased number of cells in the scratched gap after 24 hours.

TABLE 4

Results of Control (unaugmented media, AFP, DRE, AVJ, GLE, LSC, and OSC scratch assays as analyzed by ImageJ software. Values are the determined widths in mm of scratched areas at t = 0 and at 24 hours. Entries in rows marked diff. are differences between width of scratched areas at t = 0 and at 24 hours for the same well.

| | replicate 1 | replicate 2 | replicate 3 | Average | SD | SE |
|---|---|---|---|---|---|---|
| Control t = 0 | 28.90 | 29.98 | 29.87 | 29.58 | 0.59 | 0.34 |
| Control t = 24 | 27.89 | 27.75 | 27.65 | 27.76 | 0.12 | 0.07 |
| Control diff. | 1.01 | 2.23 | 2.22 | 1.82 | 0.57 | 0.33 |
| AFP, t = 0 | | | | | | |
| 100 μg/mL | 29.21 | 29.09 | 28.9 | 29.07 | 0.16 | 0.09 |
| 250 μg/mL | 28.9 | 29.78 | 29.88 | 29.52 | 0.54 | 0.31 |
| AFP, t = 24 | | | | | | |
| 100 μg/mL | 26.78 | 25.65 | 25.54 | 25.99 | 0.69 | 0.4 |
| 250 μg/mL | 25.67 | 24.32 | 25.67 | 25.22 | 0.78 | 0.45 |
| AFP diff. | | | | | | |
| 100 μg/mL | 2.43 | 3.44 | 3.36 | 3.08 | 0.46 | 0.26 |
| 250 μg/mL | 3.23 | 5.46 | 4.21 | 4.30 | 0.91 | 0.53 |
| DRE, t = 0 | | | | | | |
| 100 μg/mL | 28.92 | 28.78 | 28.77 | 28.82 | 0.08 | 0.05 |
| 250 μg/mL | 28.9 | 29 | 28.76 | 28.89 | 0.12 | 0.07 |
| DRE, t = 24 | | | | | | |
| 100 μg/mL | 26.21 | 26.55 | 27.21 | 26.66 | 0.51 | 0.29 |
| 250 μg/mL | 26.22 | 25.43 | 25.44 | 25.7 | 0.45 | 0.26 |
| DRE diff. | | | | | | |
| 100 μg/mL | 2.71 | 2.23 | 1.56 | 2.17 | 0.47 | 0.27 |
| 250 μg/mL | 2.68 | 3.57 | 3.32 | 3.19 | 0.37 | 0.22 |
| AVJ, t = 0 | | | | | | |
| 100 μg/mL | 28.97 | 29.29 | 28.78 | 29.18 | 0.53 | 0.31 |
| 250 μg/mL | 28.79 | 28.09 | 28.94 | 28.61 | 0.45 | 0.26 |
| AVJ, t = 24 | | | | | | |
| 100 μg/mL | 25.67 | 26.77 | 26.45 | 26.3 | 0.57 | 0.33 |
| 250 μg/mL | 23.67 | 23.21 | 28.94 | 25.27 | 3.18 | 1.84 |
| AVJ diff. | | | | | | |
| 100 μg/mL | 3.3 | 2.52 | 2.33 | 2.72 | 0.42 | 0.24 |
| 250 μg/mL | 5.12 | 4.88 | 0 | 3.33 | 2.36 | 1.36 |
| GLE, t = 0 | | | | | | |
| 100 μg/mL | 28.88 | 29.9 | 28.97 | 29.53 | 0.56 | 0.33 |
| 250 μg/mL | 29.09 | 29.78 | 28.9 | 29.26 | 0.46 | 0.27 |
| GLE, t = 24 | | | | | | |
| 100 μg/mL | 27.89 | 26.98 | 26.56 | 27.14 | 0.68 | 0.39 |
| 250 μg/mL | 24.56 | 23.45 | 24.87 | 24.29 | 0.75 | 0.43 |
| GLE diff. | | | | | | |
| 100 μg/mL | 0.99 | 2.92 | 2.41 | 2.11 | 0.82 | 0.47 |
| 250 μg/mL | 4.53 | 6.33 | 4.03 | 4.96 | 0.99 | 0.57 |

TABLE 4-continued

Results of Control (unaugmented media, AFP, DRE, AVJ, GLE, LSC, and OSC scratch assays as analyzed by ImageJ software. Values are the determined widths in mm of scratched areas at t = 0 and at 24 hours. Entries in rows marked diff. are differences between width of scratched areas at t = 0 and at 24 hours for the same well.

|  | replicate 1 | replicate 2 | replicate 3 | Average | SD | SE |
|---|---|---|---|---|---|---|
| LSC, t = 0 |  |  |  |  |  |  |
| 100 µg/mL | 28.78 | 29.87 | 29.56 | 29.4 | 0.56 | 0.32 |
| 250 µg/mL | 28.77 | 29.77 | 29.78 | 29.44 | 0.58 | 0.34 |
| LSC, t = 24 |  |  |  |  |  |  |
| 100 µg/mL | 27.65 | 27.16 | 27.89 | 27.57 | 0.37 | 0.21 |
| 250 µg/mL | 24.32 | 24.33 | 25.21 | 24.62 | 0.51 | 0.30 |
| LSC diff. |  |  |  |  |  |  |
| 100 µg/mL | 1.13 | 2.71 | 1.67 | 1.84 | 0.66 | 0.38 |
| 250 µg/mL | 4.45 | 5.44 | 4.57 | 4.82 | 0.44 | 0.25 |
| OSC, t = 0 |  |  |  |  |  |  |
| 100 µg/mL | 28.9 | 28.78 | 29 | 28.89 | 0.11 | 0.06 |
| 250 µg/mL | 28.97 | 28.98 | 28.78 | 28.91 | 0.11 | 0.07 |
| OSC, t = 24 |  |  |  |  |  |  |
| 100 µg/mL | 25.43 | 26.21 | 24.43 | 25.36 | 0.89 | 0.52 |
| 250 µg/mL | 24.32 | 24.44 | 23.21 | 23.99 | 0.68 | 0.39 |
| OSC diff. |  |  |  |  |  |  |
| 100 µg/mL | 3.47 | 2.57 | 4.57 | 3.54 | 0.82 | 0.47 |
| 250 µg/mL | 4.65 | 4.54 | 5.57 | 4.92 | 0.46 | 0.27 |

| Treatment | Mean ratio | standard deviation |
|---|---|---|
| AFP |  |  |
| 100 µg/mL | 1.69 | 0.35 |
| 250 µg/mL | 2.36 | 0.38 |
| DRE |  |  |
| 100 µg/mL | 1.19 | 0.38 |
| 250 µg/mL | 1.75 | 0.34 |
| AVJ |  |  |
| 100 µg/mL | 1.49 | 0.35 |
| 250 µg/mL | 1.83 | 0.77 |
| GLE |  |  |
| 100 µg/mL | 1.16 | 0.50 |
| 250 µg/mL | 2.73 | 0.37 |
| LSC |  |  |
| 100 µg/mL | 1.01 | 0.48 |
| 250 µg/mL | 2.65 | 0.33 |
| OSC |  |  |
| 100 µg/mL | 1.94 | 0.39 |
| 250 µg/mL | 2.70 | 0.33 |

Table 5 shows results calculated from the data of from Table 4 where each value was calculated by forming a ratio of the mean differences of Table 4 to the mean differences of the control wells. Standard deviations were calculated by error propagation assuming errors were uncorrelated. These summary results showed a higher degree of scratch closure for the treated wells, with a higher degree of closure at the higher plant material concentrations. The number of replicates may not be sufficient to show reasonable statistical significance for the effects in all cases. AFP, GLE, LSC, and OSC had the most outstanding performance in promoting regeneration under the conditions of this assay. Each of the plant stem cell extracts outperformed all but one of the non-stem-cell materials.

Figure 4:
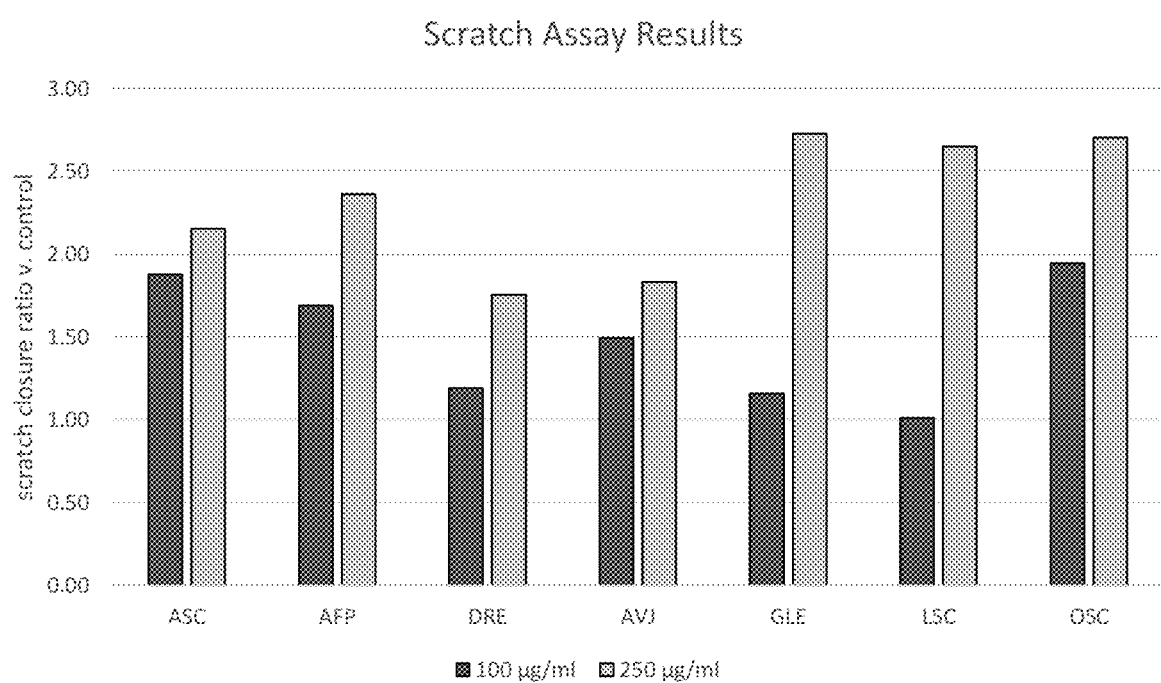

FIG. 4 is a summary graphical representation of the control-ratioed scratch assay results (including the ASC results from Example 4). Note the consistent values where scratch results for treated cells are greater than one, particularly at the higher tested concentrations, with the higher concentration plant stem cell extracts consistently promoting regeneration in this assay.

Example 6: TNF-α Cytokine Release Assay

In an inflammatory reaction, activated cells (such as macrophages) release a variety of pro-inflammatory cytokines (such as tumor necrosis factor alpha (TNF-α). The released cytokines can be assayed as a measure of inflammatory activity. To evaluate the anti-inflammatory role of apple stem cell extracts, mouse RAW 264.7 cell lines mouse macrophages were used as an adherent monolayer on petri dishes. These cells could be harvested easily without damage caused by enzymes or cell scrapers. The macrophages were stimulated in suspension with lipopolysaccharide (LPS) to initiate an inflammatory response. Cells were seeded into 12-well cell culture plates containing the apple stem cell extract treatment materials. After 16-18 hours, the medium conditioned by the macrophages was harvested and the cytokine profile in the medium determined with enzyme-linked immunosorbent assays (ELISA) by measuring TNF-α levels.

Method: Three concentration of ASC (6.25, 12.5 and 25 µg/mL in media) were tested for the anti-inflammatory effect. RAW 264.7 mouse macrophage cells were maintained in DMEM containing Glutamax supplemented with 10% FBS, penicillin (100 U/ml) and streptomycin (100 µg/ml). The macrophages treated with LPS (1:500 dilution of a 0.1 mg/ml solution of LPS in phosphate buffered saline (PBS)) to produce a pro-inflammatory response. The ASC treatment was performed with a final concentration of $1 \times 10^5$ macrophages in wells of a 12-well plate. The cytokine assay was performed using a TNF-α ELISA from R&D Systems of Minneapolis, Minn.

Figure 5:
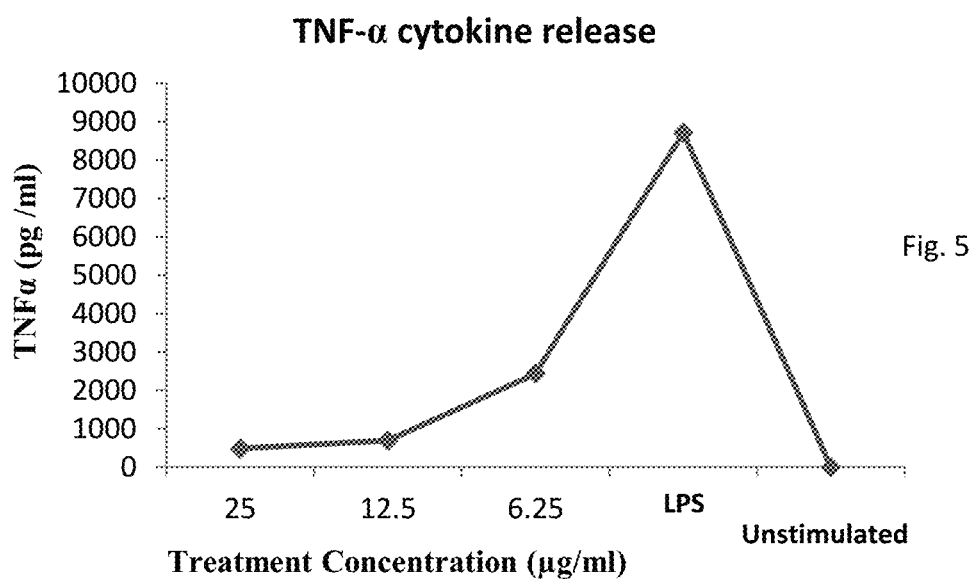

Results indicated (Table 6, FIG. 5) that LPS alone produced an inflammatory response more than 1000 times that of unstimulated cells as measured by TNF-α expression. Treatment with ASC on the induced macrophages showed a dose-dependent decrease of TNF-α expression. ASC concentrations of 6.25, 12.5, and 25 µg/mL reduced TNF-α activity in the induced cells by 72.1, 92.1 and 94.5%, respectively. This reduced TNF-α at doses of 12.5 and 25 µg/ml was statistically significant with p≤0.05 for 25 µg/ml and p≤0.02 in 12.5 µg/ml. The apple stem cell extracts thus exerted an anti-inflammatory effect on the activated macrophage cells.

TABLE 6

Results of TNF-α release assay showing anti-inflammatory effects of apple stem cell extracts on mouse RAW 264.7 macrophage cell line cells.

| Apple Stem Cell Extract Conc. (µg/ml) | TNF-α (pg/ml) | percent inhibition vs. LPS |
|---|---|---|
| 25 | 481.89 | 94.5 |
| 12.5 | 687.9 | 92.1 |
| 6.25 | 2432.89 | 72.1 |
| LPS | 8712.63 | 0 |
| unstimulated | 6.45 | |

Values shown are averages of three sets of experiments.
ASC extracts dramatically reduced inflammatory responses in the target cells, as exemplified by reduced TNF-α release (greater inhibition of inflammation).

Example 7: MTT Cell Proliferation Assay I

The MTT Cell Proliferation assay determines cell survival following apple stem cell extract treatment. The purpose was to evaluate the potential anti-tumor activity of apple stem cell extracts as well as to evaluate the dose-dependent cell cytotoxicity.

Principle: Treated cells are exposed to 3-(4,5-dimethythiazol-2-yl)-2,5-diphenyl tetrazolium bromide (MTT). MTT enters living cells and passes into the mitochondria where it is reduced by mitochondrial succinate dehydrogenase to an insoluble, colored (dark purple) formazan product. The cells are then solubilized with DMSO and the released, solubilized formazan is measured spectrophotometrically. The MTT assay measures cell viability based on the generation of reducing equivalents. Reduction of MTT only occurs in metabolically active cells, so the level of activity is a measure of the viability of the cells. The percentage cell viability is calculated against untreated cells.

Method: A549 and NCI-H520 lung cancer cell lines and L132 lung epithelial cell line were used to determine the plant stem cell treatment tumor-specific cytotoxicity. The cell lines were maintained in Minimal Essential Media supplemented with 10% FBS, penicillin (100 U/ml) and streptomycin (100 µg/ml) in a 5% $CO_2$ at 37 Celsius. Cells were seeded at $5 \times 10^3$ cells/well in 96-well plates and incubated for 48 hours. Triplicates of eight concentrations of the apple stem cell extract were added to the media and cells were incubated for 24 hours. This was followed by removal of media and subsequent washing with the phosphate saline solution. Cell proliferation was measured using the MTT Cell Proliferation Kit I (Boehringer Mannheim, Indianapolis, Ind.). New medium containing 50 µl of MTT solution (5 mg/ml) was added to each well and cultures were incubated a further 4 hours. Following this incubation, DMSO was added and the cell viability was determined by the absorbance at 570 nm by a microplate reader.

In order to determine the effectiveness of apple stem cell extracts as an anti-tumor biological agent, an MTT assay was carried out and IC50 values were calculated. IC50 is the half maximal inhibitory function concentration of a drug or compound required to inhibit a biological process. The measured process is cell death.

Results: ASC-treated Human lung adenocarcinoma cell line A549.

TABLE 7

Results of cytotoxicity of apple stem cell extract on lung cancer cell line A549 as measured by MTT assay (performed in triplicate). Values of replicates are % of cell death.

| Concentration* (µg/ml) | replicate 1 | replicate 2 | replicate 3 | Mean of replicates | SD | SEM | % Live Cells |
|---|---|---|---|---|---|---|---|
| 250 | 93.18 | 90.86 | 90.34 | 91.46 | 1.51 | 0.87 | 8.54 |
| 100 | 86.88 | 85.18 | 85.69 | 85.92 | 0.87 | 0.50 | 14.08 |
| 50 | 80.58 | 79.49 | 81.04 | 80.37 | 0.80 | 0.46 | 19.63 |
| 25 | 74.28 | 73.81 | 76.39 | 74.83 | 1.38 | 0.79 | 25.17 |
| 12.5 | 67.98 | 68.13 | 71.75 | 69.28 | 2.13 | 1.23 | 30.72 |
| 6.25 | 61.67 | 62.45 | 67.10 | 63.74 | 2.93 | 1.69 | 36.26 |
| 3.125 | 55.37 | 56.77 | 62.45 | 58.20 | 3.75 | 2.16 | 41.80 |
| 1.562 | 49.07 | 51.08 | 57.80 | 52.65 | 4.57 | 2.64 | 47.35 |
| 0.781 | 42.77 | 45.40 | 53.15 | 47.11 | 5.40 | 3.12 | 52.89 |

Results: ASC-treated Human squamous carcinoma cell line NCI-H520.

TABLE 8

Results of cytotoxicity of apple stem cell extract on lung cancer cell line NCI-H520 as measured by MTT assay (performed in triplicate). Values of replicates are % of cell death.

| Concentration* (µg/ml) | replicate 1 | replicate 2 | replicate 3 | Mean of replicates | SD | SEM | % Live cell |
|---|---|---|---|---|---|---|---|
| 250 | 88.28 | 89.29 | 87.73 | 88.43 | 0.79 | 0.46 | 11.57 |
| 100 | 78.13 | 79.19 | 78.13 | 78.48 | 0.61 | 0.35 | 21.52 |
| 50 | 67.98 | 69.09 | 68.54 | 68.54 | 0.56 | 0.32 | 31.46 |
| 25 | 57.83 | 58.99 | 58.94 | 58.59 | 0.66 | 0.38 | 41.41 |
| 12.5 | 47.68 | 48.89 | 49.34 | 48.64 | 0.86 | 0.50 | 51.36 |
| 6.25 | 37.53 | 38.79 | 39.75 | 38.69 | 1.11 | 0.64 | 61.31 |
| 3.125 | 27.37 | 28.69 | 30.15 | 28.74 | 1.39 | 0.80 | 71.26 |
| 1.562 | 17.22 | 18.59 | 20.56 | 18.79 | 1.68 | 0.97 | 81.21 |
| 0.781 | 7.07 | 8.48 | 10.96 | 8.84 | 1.97 | 1.14 | 91.16 |

Results: ASC-treated lung epithelial cell line L132.

TABLE 9

Results of cytotoxicity of apple stem cell extract on lung epithelial cell line L132 as measured by MTT assay (performed in triplicate). Values of replicates are % of cell death.

| Concentration* (µg/ml) | replicate 1 | replicate 2 | replicate 3 | Mean of replicates | SD | SEM | % Live cell |
|---|---|---|---|---|---|---|---|
| 250 | 39.51 | 42.52 | 44.03 | 42.02 | 2.30 | 1.33 | 57.98 |
| 100 | 32.93 | 34.44 | 33.69 | 33.69 | 0.75 | 0.44 | 66.31 |
| 50 | 30.60 | 28.94 | 30.52 | 30.02 | 0.94 | 0.54 | 69.98 |
| 25 | 27.96 | 27.81 | 27.13 | 27.63 | 0.44 | 0.25 | 72.37 |
| 12.5 | 25.62 | 25.55 | 25.40 | 25.52 | 0.12 | 0.07 | 74.48 |
| 6.25 | 23.13 | 20.87 | 18.61 | 20.87 | 2.26 | 1.31 | 79.13 |
| 3.125 | 13.34 | 11.08 | 11.83 | 12.08 | 1.15 | 0.66 | 87.92 |
| 1.562 | 6.56 | 7.31 | 9.57 | 7.81 | 1.57 | 0.91 | 92.19 |
| 0.781 | 8.06 | 4.30 | 3.54 | 5.30 | 2.42 | 1.40 | 94.70 |

Summary Results: cytotoxicity of apple stem cell extracts.

TABLE 10

IC50 values of the apple stem cell extracts on the on the target cell lines as determined by MTT assay.

| Target Cell Line | IC50 |
|---|---|
| A549 | 12.58 |
| NCI-H520 | 10.21 |
| L132 | 127.46 |

Figure 6:
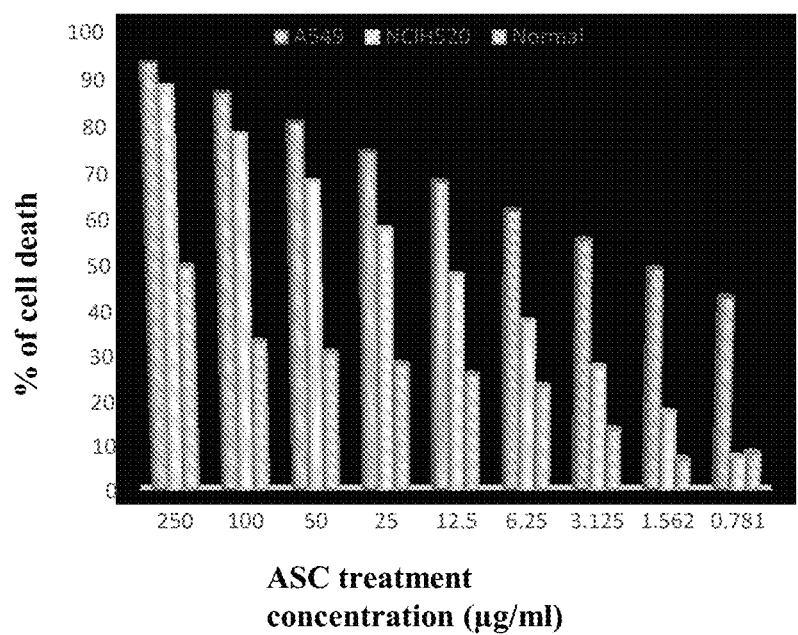

Apple stem cell extracts killed lung cancer cells lines A549 and NCI-H520 at relatively low doses: IC50s were 12.58 and 10.21 µg/ml respectively as compared to 127.46 µg/ml for the lung epithelial cell line L132. Near complete anti-tumor activity was seen at a dose of 250 µg/ml in both the lung cancer cell lines. This same dose spared more than one half of the L132 cells. See Tables 7-10. The data revealed that apple stem cell extract is cytotoxic to lung cancer cells while sparing lung epithelial cells. FIG. 6 shows a graphical representation of cytotoxicity activity of apple stem cell extracts on lung tumor cell lines A549, NCIH520 and on L132 lung epithelial cell line (marked "Normal"). The Y-axis is the mean % of cells killed by the indicated treatment compared to unexposed cells. The difference in cytotoxicity levels was statistically significant at $p \leq 0.05$.

Example 9: MTT Cell Proliferation Assay II

The experiment of Example 7 was repeated substituting other plant materials for ASC. Plant stem cell materials included Dandelion Root Extract (DRE), *Aloe Vera* Juice (AVJ), Apple Fiber Powder (AFP), *Ginkgo* Leaf Extract (GLE), Lingonberry Stem Cells (LSC), Orchid Stem Cells (OSC) as described in Examples 1 and 2. The concentrations of plant materials used were nominally 250, 100, 50, 25, 6.25, 3.125, 1.562, and 0.781 µg/mL. These materials were tested only for cells the human lung epithelial cell line L132 (as a proxy for normal epithelial cells) and for cells of the human lung adenocarcinoma cell line A549 (as a proxy for lung cancer cells).

A549 cells lung cancer cell line cytotoxicity results for each of the treatment materials.

DRE-treated lung cancer cell line A549 cells.

TABLE 11

Triplicate results of cell death of DRE-treated A549 cells measured by MTT assay. Percentage of live cells calculated as 100% - Mean of triplicates.

| Concentration (µg/mL)-DRE-treated A549 | % of cell death | | | Mean | SD | SEM | % Live cell |
|---|---|---|---|---|---|---|---|
| 250 | 80.43 | 76.40 | 74.84 | 77.23 | 2.89 | 1.67 | 22.77 |
| 100 | 67.60 | 75.26 | 63.77 | 68.88 | 5.85 | 3.38 | 31.12 |
| 50 | 65.32 | 62.94 | 59.94 | 62.73 | 2.70 | 1.56 | 37.27 |
| 25 | 56.83 | 57.97 | 48.14 | 54.31 | 5.38 | 3.11 | 45.69 |
| 6.25 | 55.59 | 49.69 | 49.17 | 51.48 | 3.57 | 2.06 | 48.52 |
| 3.125 | 51.76 | 48.45 | 45.34 | 48.52 | 3.21 | 1.85 | 51.48 |
| 1.562 | 43.69 | 44.00 | 36.02 | 41.24 | 4.52 | 2.61 | 58.76 |
| 0.781 | 37.47 | 26.19 | 19.57 | 27.74 | 9.05 | 5.23 | 72.26 |

AVJ-treated lung cancer cell line A549 cells.

TABLE 12

Triplicate results of cell death of AVJ-treated A549 cells measured by MTT assay. Percentage of live cells calculated as 100% - Mean of triplicates.

| Concentration (µg/mL)-AVJ-treated A549 | % of cell death | | | Mean | SD | SEM | % Live cell |
|---|---|---|---|---|---|---|---|
| 250 | 76.81 | 78.16 | 75.88 | 76.95 | 1.14 | 0.66 | 23.05 |
| 100 | 76.40 | 75.26 | 73.71 | 75.12 | 1.35 | 0.78 | 24.88 |
| 50 | 65.32 | 66.15 | 59.94 | 63.80 | 3.37 | 1.95 | 36.20 |
| 25 | 50.10 | 48.45 | 56.63 | 51.73 | 4.32 | 2.50 | 48.27 |
| 6.25 | 47.52 | 46.38 | 46.17 | 46.69 | 0.72 | 0.42 | 53.31 |
| 3.125 | 39.86 | 38.61 | 43.79 | 40.75 | 2.70 | 1.56 | 59.25 |
| 1.562 | 32.40 | 19.77 | 30.54 | 27.57 | 6.82 | 3.94 | 72.43 |
| 0.781 | 20.50 | 15.63 | 32.19 | 22.77 | 8.51 | 4.92 | 77.23 |

AFP-treated lung cancer cell line A549 cells.

TABLE 13

Triplicate results of cell death of AFP-treated A549 cells measured by MTT assay. Percentage of live cells calculated as 100% - Mean of triplicates.

| Concentration (µg/mL)-AFP-treated A549 | % of cell death | | | Mean | SD | SEM | % Live cell |
|---|---|---|---|---|---|---|---|
| 250 | 86.13 | 87.99 | 86.65 | 86.92 | 0.96 | 0.56 | 13.08 |
| 100 | 79.50 | 81.06 | 82.09 | 80.88 | 1.30 | 0.75 | 19.12 |
| 50 | 73.60 | 72.46 | 71.33 | 72.46 | 1.14 | 0.66 | 27.54 |
| 25 | 68.01 | 67.70 | 66.98 | 67.56 | 0.53 | 0.31 | 32.44 |
| 6.25 | 60.87 | 62.11 | 60.77 | 61.25 | 0.75 | 0.43 | 38.75 |
| 3.125 | 49.48 | 51.76 | 50.72 | 50.66 | 1.14 | 0.66 | 49.34 |
| 1.562 | 40.06 | 41.72 | 47.00 | 42.93 | 3.62 | 2.09 | 57.07 |
| 0.781 | 39.23 | 37.78 | 36.85 | 37.96 | 1.20 | 0.69 | 62.04 |

GLE-treated lung cancer cell line A549 cells.

TABLE 14

Triplicate results of cell death of GLE-treated A549 cells measured by MTT assay. Percentage of live cells calculated as 100% - Mean of triplicates.

| Concentration (µg/mL)-GLE-treated A549 | % of cell death | | | Mean | SD | SEM | % Live cell |
|---|---|---|---|---|---|---|---|
| 250 | 88.42 | 91.49 | 90.44 | 90.12 | 1.56 | 0.90 | 9.88 |
| 100 | 84.39 | 83.77 | 83.16 | 83.77 | 0.61 | 0.35 | 16.23 |
| 50 | 79.47 | 81.58 | 76.75 | 79.27 | 2.42 | 1.40 | 20.73 |

TABLE 14-continued

Triplicate results of cell death of GLE-treated A549 cells measured by MTT assay. Percentage of live cells calculated as 100% - Mean of triplicates.

| Concentration (μg/mL)-GLE-treated A549 | % of cell death | | | Mean | SD | SEM | % Live cell |
|---|---|---|---|---|---|---|---|
| 25 | 73.60 | 72.54 | 71.40 | 72.51 | 1.10 | 0.63 | 27.49 |
| 6.25 | 62.89 | 63.68 | 59.91 | 62.16 | 1.99 | 1.15 | 37.84 |
| 3.125 | 50.18 | 54.47 | 51.84 | 52.16 | 2.17 | 1.25 | 47.84 |
| 1.562 | 46.93 | 44.30 | 43.33 | 44.85 | 1.86 | 1.07 | 55.15 |
| 0.781 | 39.56 | 39.39 | 40.96 | 39.97 | 0.87 | 0.50 | 60.03 |

LSC-treated lung cancer cell line A549 cells.

TABLE 15

Triplicate results of cell death of LSC-treated A549 cells measured by MTT assay. Percentage of live cells calculated as 100% - Mean of triplicates.

| Concentration (μg/mL) LSC treated A549 | % of cell death | | | Mean | SD | SEM | % Live cell |
|---|---|---|---|---|---|---|---|
| 250 | 77.54 | 78.85 | 78.20 | 78.20 | 0.65 | 0.38 | 21.80 |
| 100 | 77.14 | 76.04 | 76.59 | 76.59 | 0.55 | 0.32 | 23.41 |
| 50 | 66.42 | 68.52 | 66.82 | 67.25 | 1.12 | 0.65 | 32.75 |
| 25 | 59.80 | 67.22 | 64.16 | 63.73 | 3.73 | 2.15 | 36.27 |
| 6.25 | 50.53 | 48.82 | 48.07 | 49.14 | 1.26 | 0.73 | 50.86 |
| 3.125 | 41.14 | 43.60 | 42.72 | 42.49 | 1.24 | 0.72 | 57.51 |
| 1.562 | 39.47 | 39.74 | 40.61 | 39.94 | 0.60 | 0.34 | 60.06 |
| 0.781 | 38.55 | 31.83 | 36.79 | 35.72 | 3.48 | 2.01 | 64.28 |

OSC-treated lung cancer cell line A549 cells.

TABLE 16

Triplicate results of cell death of OSC-treated A549 cells measured by MTT assay. Percentage of live cells calculated as 100% - Mean of triplicates.

| Concentration (μg/mL) OSC-treated A549 | % of cell death | | | Mean | SD | SEM | % Live cell |
|---|---|---|---|---|---|---|---|
| 250 | 70.84 | 65.57 | 71.49 | 69.30 | 3.25 | 1.87 | 30.70 |
| 100 | 48.81 | 50.91 | 57.28 | 52.33 | 4.41 | 2.55 | 47.67 |
| 50 | 46.59 | 49.60 | 53.33 | 49.84 | 3.38 | 1.95 | 50.16 |
| 25 | 38.77 | 40.81 | 36.58 | 38.72 | 2.11 | 1.22 | 61.28 |
| 6.25 | 35.74 | 40.79 | 41.05 | 39.19 | 3.00 | 1.73 | 60.81 |
| 3.125 | 34.55 | 33.68 | 37.02 | 35.08 | 1.73 | 1.00 | 64.92 |
| 1.562 | 33.86 | 33.44 | 27.63 | 31.64 | 3.48 | 2.01 | 68.36 |
| 0.781 | 21.32 | 20.00 | 34.82 | 25.38 | 8.21 | 4.74 | 74.62 |

L132 cells ("normal" lung epithelial cell line) cytotoxicity results for each of the treatment materials.

DRE-treated lung epithelial cell line L132 cells.

TABLE 17

Triplicate results of cell death of DRE-treated L132 cells measured by MTT assay. Percentage of live cells calculated as 100% - Mean of triplicates.

| Concentration (μg/mL) DRE-treated L132 | % of cell death | | | Mean | SD | SEM | % Live cell |
|---|---|---|---|---|---|---|---|
| 250 | 86.66 | 86.61 | 86.66 | 86.64 | 0.03 | 0.02 | 13.36 |
| 100 | 76.29 | 77.39 | 76.84 | 76.84 | 0.55 | 0.32 | 23.16 |
| 50 | 65.92 | 68.17 | 67.01 | 67.03 | 1.13 | 0.65 | 32.97 |
| 25 | 55.54 | 58.95 | 57.19 | 57.23 | 1.70 | 0.98 | 42.77 |
| 6.25 | 45.17 | 49.73 | 47.37 | 47.42 | 2.28 | 1.32 | 52.58 |

TABLE 17-continued

Triplicate results of cell death of DRE-treated L132 cells measured by MTT assay. Percentage of live cells calculated as 100% - Mean of triplicates.

| Concentration (μg/mL) DRE-treated L132 | % of cell death | | | Mean | SD | SEM | % Live cell |
|---|---|---|---|---|---|---|---|
| 3.125 | 34.80 | 40.50 | 37.54 | 37.61 | 2.85 | 1.65 | 62.39 |
| 1.562 | 24.42 | 31.28 | 27.72 | 27.81 | 3.43 | 1.98 | 72.19 |
| 0.781 | 14.05 | 22.06 | 17.89 | 18.00 | 4.01 | 2.31 | 82.00 |

AVJ-treated lung epithelial cell line L132 cells.

TABLE 18

Triplicate results of cell death of AVJ-treated L132 cells measured by MTT assay. Percentage of live cells calculated as 100% - Mean of triplicates AFP-treated lung epithelial cell line L132 cells.

| Concentration (μg/mL) AVJ-treated L132 | % of cell death | | | Mean | SD | SEM | % Live cell |
|---|---|---|---|---|---|---|---|
| 250 | 57.03 | 55.93 | 53.62 | 55.53 | 1.74 | 1.00 | 44.47 |
| 100 | 50.99 | 49.78 | 47.04 | 49.27 | 2.03 | 1.17 | 50.73 |
| 50 | 44.95 | 43.63 | 40.45 | 43.01 | 2.31 | 1.34 | 56.99 |
| 25 | 38.91 | 37.49 | 33.86 | 36.75 | 2.60 | 1.50 | 63.25 |
| 6.25 | 32.88 | 31.34 | 27.28 | 30.50 | 2.89 | 1.67 | 69.50 |
| 3.125 | 26.84 | 25.19 | 20.69 | 24.24 | 3.18 | 1.84 | 75.76 |
| 1.562 | 20.80 | 19.05 | 14.11 | 17.98 | 3.47 | 2.00 | 82.02 |
| 0.781 | 14.76 | 12.90 | 7.52 | 11.73 | 3.76 | 2.17 | 88.27 |

AFP-treated lung epithelial cell line L132 cells.

TABLE 19

Triplicate results of cell death of AFP-treated L132 cells measured by MTT assay. Percentage of live cells calculated as 100% - Mean of triplicates AFP-treated lung epithelial cell line L132 cells.

| Concentration (μg/mL) AFP-treated L132 | % of cell death | | | Mean | SD | SEM | % Live cell |
|---|---|---|---|---|---|---|---|
| 250 | 56.15 | 55.43 | 57.19 | 56.26 | 0.88 | 0.51 | 43.74 |
| 100 | 49.95 | 48.24 | 47.64 | 48.61 | 1.20 | 0.69 | 51.39 |
| 50 | 43.74 | 41.05 | 38.09 | 40.96 | 2.83 | 1.63 | 59.04 |
| 25 | 37.54 | 33.86 | 28.54 | 33.32 | 4.53 | 2.61 | 66.68 |
| 6.25 | 31.34 | 26.67 | 18.99 | 25.67 | 6.24 | 3.60 | 74.33 |
| 3.125 | 25.14 | 19.48 | 9.44 | 18.02 | 7.95 | 4.59 | 81.98 |
| 1.562 | 18.94 | 12.29 | 10.87 | 14.03 | 4.31 | 2.49 | 85.97 |
| 0.781 | 12.73 | 5.10 | 6.81 | 8.21 | 4.00 | 2.31 | 91.79 |

GLE-treated lung epithelial cell line L132 cells.

TABLE 20

Triplicate results of cell death of GLE-treated L132 cells measured by MTT assay. Percentage of live cells calculated as 100% - Mean of triplicates AFP-treated lung epithelial cell line L132 cells.

| Concentration (μg/mL) GLE-treated L132 | % of cell death | | | Mean | SD | SEM | % Live cell |
|---|---|---|---|---|---|---|---|
| 250 | 84.42 | 83.20 | 83.08 | 83.57 | 0.74 | 0.43 | 16.43 |
| 100 | 80.05 | 79.29 | 78.59 | 79.31 | 0.73 | 0.42 | 20.69 |
| 50 | 72.75 | 71.59 | 74.10 | 72.81 | 1.26 | 0.72 | 27.19 |
| 25 | 80.05 | 81.86 | 79.99 | 80.63 | 1.06 | 0.61 | 19.37 |
| 6.25 | 68.26 | 70.13 | 68.26 | 68.88 | 1.08 | 0.62 | 31.12 |
| 3.125 | 60.62 | 63.07 | 60.62 | 61.44 | 1.41 | 0.82 | 38.56 |
| 1.562 | 48.07 | 48.77 | 48.83 | 48.56 | 0.42 | 0.24 | 51.44 |
| 0.781 | 46.27 | 45.57 | 46.67 | 46.17 | 0.56 | 0.32 | 53.83 |

LSC-treated lung epithelial cell line L132 cells.

TABLE 21

Triplicate results of cell death of LSC-treated L132 cells measured by MTT assay. Percentage of live cells calculated as 100% - Mean of triplicates AFP-treated lung epithelial cell line L132 cells.

| Concentration (μg/mL) LSC-treated L132 | % of cell death | | | Mean | SD | SEM | % Live cell |
|---|---|---|---|---|---|---|---|
| 250 | 86.41 | 85.82 | 85.76 | 86.00 | 0.35 | 0.20 | 14.00 |
| 100 | 81.21 | 81.27 | 79.99 | 80.82 | 0.72 | 0.42 | 19.18 |
| 50 | 75.96 | 74.74 | 73.51 | 74.74 | 1.23 | 0.71 | 25.26 |
| 25 | 74.74 | 72.75 | 71.47 | 72.99 | 1.65 | 0.95 | 27.01 |
| 6.25 | 70.13 | 68.32 | 68.26 | 68.90 | 1.06 | 0.61 | 31.10 |
| 3.125 | 54.03 | 58.05 | 53.44 | 55.17 | 2.51 | 1.45 | 44.83 |
| 1.562 | 53.97 | 51.98 | 51.98 | 52.64 | 1.15 | 0.66 | 47.36 |
| 0.781 | 46.79 | 45.62 | 44.92 | 45.78 | 0.94 | 0.54 | 54.22 |

OSC-treated lung epithelial cell line L132 cells.

TABLE 22

Triplicate results of cell death of OSC-treated L132 cells measured by MTT assay. Percentage of live cells calculated as 100% - Mean of triplicates AFP-treated lung epithelial cell line L132 cells.

| Concentration (μg/mL) OSC-treated L132 | % of cell death | | | Mean | SD | SEM | % Live cell |
|---|---|---|---|---|---|---|---|
| 250 | 61.84 | 62.37 | 60.44 | 61.55 | 1.00 | 0.57 | 38.45 |
| 100 | 54.14 | 53.44 | 52.10 | 53.23 | 1.04 | 0.60 | 46.77 |
| 50 | 42.94 | 42.30 | 40.32 | 41.85 | 1.37 | 0.79 | 58.15 |
| 25 | 35.94 | 34.48 | 33.31 | 34.58 | 1.32 | 0.76 | 65.42 |
| 6.25 | 33.96 | 32.67 | 32.03 | 32.89 | 0.98 | 0.57 | 67.11 |
| 3.125 | 27.48 | 26.20 | 26.72 | 26.80 | 0.65 | 0.37 | 73.20 |
| 1.562 | 9.80 | 7.29 | 7.35 | 8.15 | 1.43 | 0.83 | 91.85 |
| 0.781 | 7.29 | 8.98 | 8.05 | 8.11 | 0.85 | 0.49 | 91.89 |

Calculated values.

TABLE 23

Calculated IC50 doses (ug/mL) and therapeutic ratios (IC50 for L132 cells/IC50 for A549 cells) for each treatment material. Values greater than one indicate that a material would be more selective in killing cancer cells than normal cells. ASC results imported from Example 8.

| | ASC | DRE | AVJ | AFP | GLE | LSC | OSC |
|---|---|---|---|---|---|---|---|
| A549 IC50 | 12.58 | 9.822 | 11.48 | 11.98 | 11.1 | 13.7 | 33.9 |
| L132 IC50 | 127.46 | 56.88 | 62.66 | 82.65 | 77.636 | 9.267 | 15.38 |
| Ther. Ratio | 10.1 | 5.8 | 5.5 | 6.9 | 7.0 | 0.7 | 0.5 |

These studies indicate that at least some of the materials may be effective anti-cancer agents. While some stem cell products are non-selective in this assay, ASC has outstanding selectivity compared to other materials.

Example 10: Staining of Cells

Apoptosis is a programmed cell death that eliminates physiologically redundant, physically damaged, and abnormal cells. Various staining procedures can help elucidate the mechanisms of cytotoxic effects, and in particular whether cytotoxic effects are attributable to apoptosis as compared to purely physical effects.

Ethidium bromide and acridine orange are used to visualize the cell apoptosis in a cell culture upon treatment with a biological agent or a drug. Acridine orange is a vital dye and will stain both live and dead cells. Ethidium bromide will stain only cells that have lost membrane integrity. Live cells will appear uniformly green. Early apoptotic cells will stain green and contain bright green dots in the nuclei as a consequence of chromatin condensation and nuclear fragmentation. Late apoptotic cells will also incorporate ethidium bromide and therefore stain orange, but, in contrast to necrotic cells, the late apoptotic cells will show condensed and often fragmented nuclei. Necrotic cells stain orange, but have a nuclear morphology resembling that of viable cells, with no condensed chromatin.

Calcein AM staining helps confirm cell viability. Calcein AM is a non-fluorescent, hydrophobic compound that easily permeates intact, live cells. In live cells the nonfluorescent calcein AM is converted to a green-fluorescent calcein after acetoxymethyl ester hydrolysis by intracellular esterases.

Method: A549 and NCI-H520 lung cancer cell lines were cultured in DMEM supplemented with 10% FBS, 4 mM L—glutamine, 1% penicillin/streptomycin under a fully humidified atmosphere containing 5% $CO_2$ at 37 Celsius. For experiments, cells were collected from sub confluent monolayers by trypsinization with trypsin/EDTA. Cell viability was determined using trypan blue dye exclusion staining. In all experiments. Apple stem cell extracts (6.25, 12.5, and 25 μg/mL) and 0.1% dimethyl sulfoxide vehicle controls were sterilized with UV and placed in wells of 6 well plates. Culture medium containing A549 or NCI-H520 cells were added and incubated according to the protocols below.

Calcein AM staining: The control and treated cells ($1\times10^5$ per well) were incubated with the apple stem cell extracts for 24 hours at 37 Celsius and 5% $CO_2$. The culture media was aspirated off followed by cell washing with ice cold PBS. 2 μM Calcein-AM and was added and cells incubated for 10 min at 37 Celsius. Cells were examined under a fluorescence microscope provided with a triple filter set (excitation: 400, 495, 570 nm; emission: 460, 530, 610 nm), and combined with digital camera (Canon PowerShot G8). Viability was expressed as percentage cells retaining calcein (green fluorescence) compared to the total cells counted.

Acridine orange/ethidium bromide (AO/EtBr) Staining: The control and treated cells ($3\times10^4$ per well) were incubated with the apple stem cell extracts for 48 hours at 37 Celsius and 5% $CO_2$. After incubation, cells were fixed in methanol: glacial acetic acid (3:1) for 30 min at room temperature, washed with PBS and stained with 1:1 ratio of AO/EtBr. Stained cells were immediately washed with PBS and viewed under a fluorescence microscope (Nikon, Eclipse TS100, Japan) with a magnification of ×40.

The number of cells expressing apoptotic features was counted and expressed as a fraction of the total number of cells present in the field.

Figure 7:
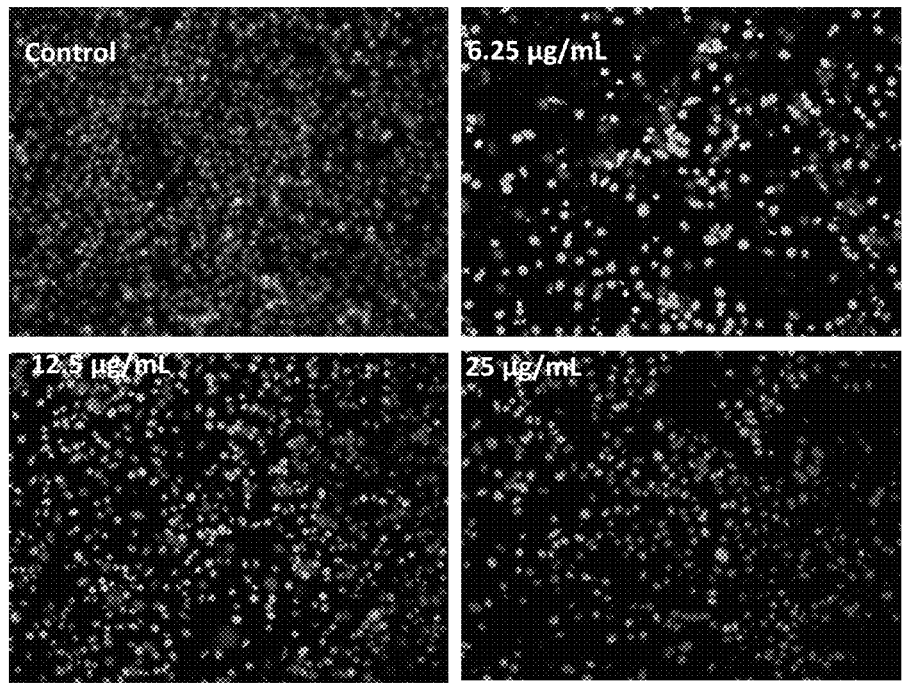
Figure 8:
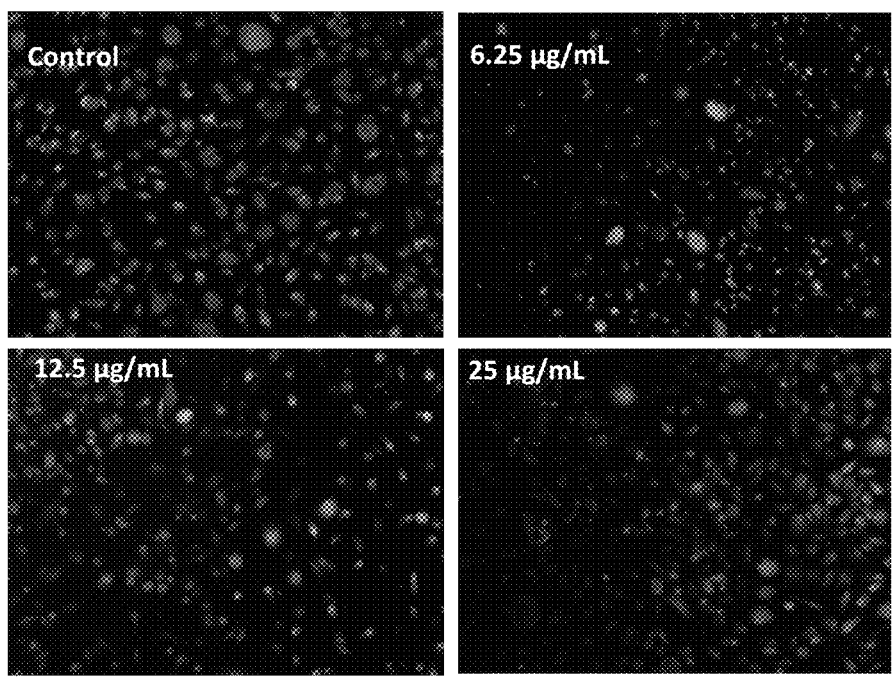

Results: FIGS. 7-8 show selected fields of treated cells stained with AO/EtBr. Each field has the associated apple stem cell extract treatment dose indicated in the corner. Note that magnification changes between images to better indicate the relative number of cells. Normal tumor cells, early and late apoptotic cells, and necrotic cells were examined using fluorescent microscopy. Early-stage apoptotic cells were marked by crescent-shaped or granular yellow-green acridine orange nuclear staining. Late-stage apoptotic cells were marked with concentrated and asymmetrically localized orange nuclear ethidium bromide staining. Necrotic cells increased in volume and showed uneven orange-red fluorescence at their periphery. Cells appeared to be in the process of disintegrating.

The percentage of apoptotic lung cancer cells of both cell lines detected by AO/EtBr staining was significant at 12.5 μg/mL of treatment dose of apple stem cell extract.

Figure 9:
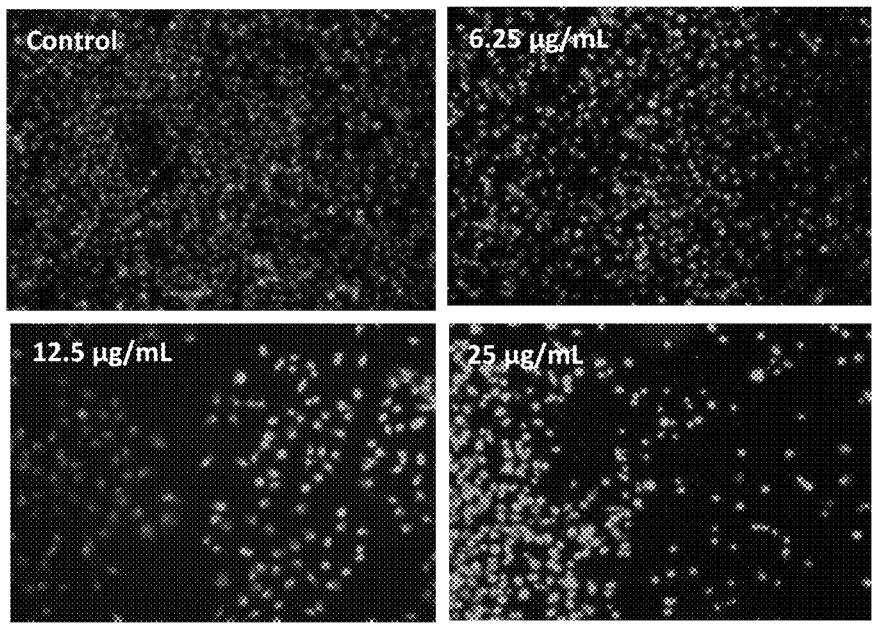
Figure 10:
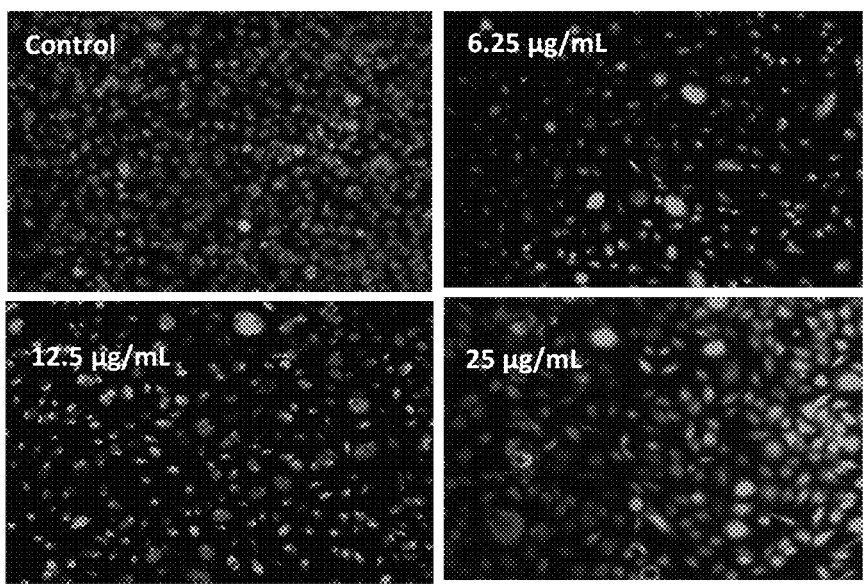

FIGS. 9-10 show selected fields of treated cells stained with Calcein AM. Each field has the associated apple stem cell extract treatment dose indicated in the corner. Note that magnification changes between images to better indicate the relative number of cells.

Consistent with the AO/EtBr staining, a dose of 12.5 μg/mL was associated with significantly fewer tumor cells exhibiting the green fluorescence indicative of viable target cells when treated with apple stem cell extract and stained with Calcein-AM. Response to the apple stem cell extracts was dose-dependent; more viable target cells were present in wells treated with lower doses of apple stem cell extracts.

These AO/EtBr and Calcein-AM staining results support that treatment with apple stem cell extracts produces apoptosis and bio-sensitivity in lung tumor cell lines.

Example 11: Lactate Dehydrogenase (LDH) Release Assay

LDH is released upon tumor cell death. Measuring released LDH can confirm cytotoxic effects. LDH is a stable cytosolic enzyme that is released from the cell upon cell lysis. The LDH assay is based on quantitatively measuring released LDH using a coupled enzymatic assay. Released LDH converts a tetrazolium salt into a red soluble formazan product which then can be measured colorimetrically. The amount of LDH released is proportional to the number of lysed cells.

Method: A549 and NCI-H520 cells were cultured as described in Example 5 and treated with varying concentrations of apple stem cell extract (0.781, 1.562, 3.125.6.25.12.5, 25, 50, 100, and 250 μg/mL) of Example 1. The cells were treated at 37 Celsius for 45-60 min, then the supernatant containing released LDH was harvested and transferred into a fresh 96-well plate. 50 μL of substrate mix was added to each well containing the transferred supernatant. The plate was incubated for 30 min at room temperature and the reaction stopped by adding 50 μL of stop solution to each well. Absorbance of the solutions was measured at 490 nm in a plate reader and the results expressed as a percentage of LDH released (n=4±S.D.) compared to maximum LDH released from lysed control cells.

Figure 11:
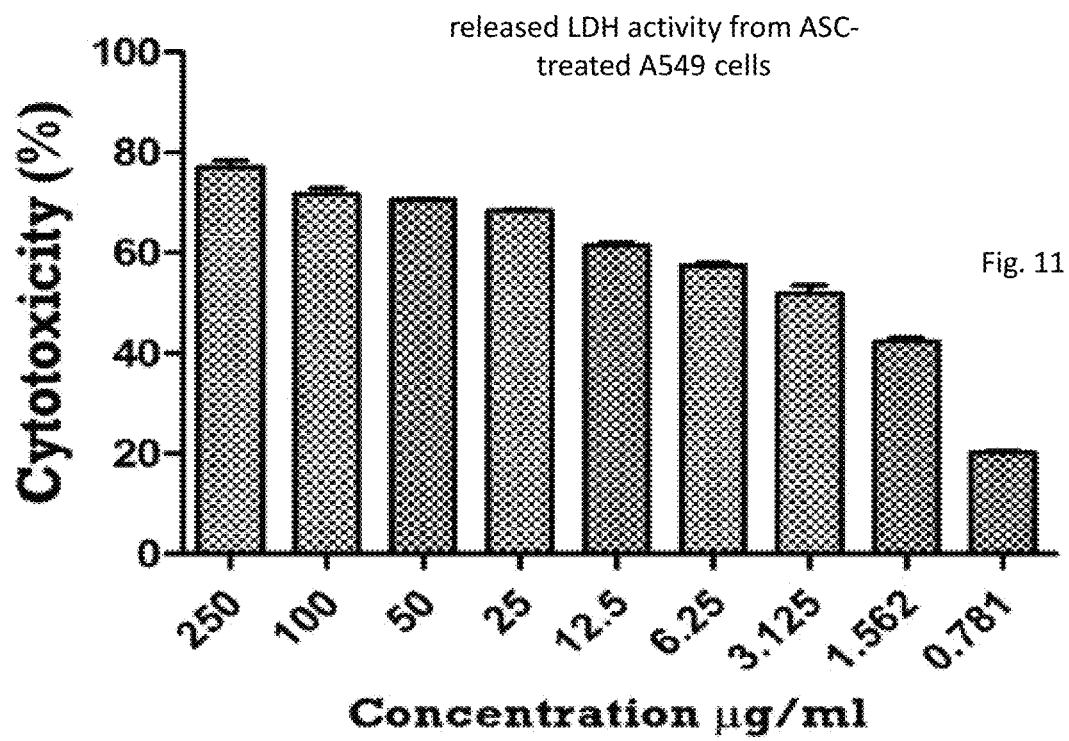
Figure 12:
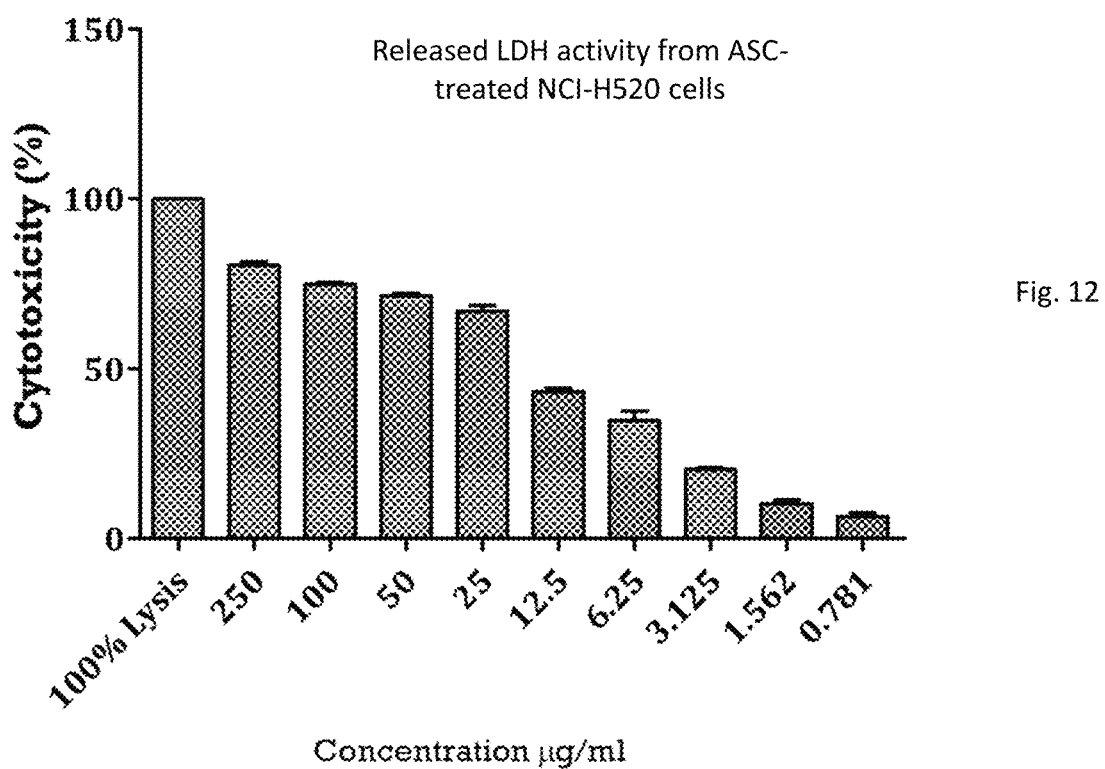

Results: Significant released LDH activity was observed with doses of 100 and 250 μg/ml correlating to about 78% cell cytotoxicity in both the lung cancer cell lines (FIG. 11 for A549 cells and FIG. 12 for NCI-H520 cells). The data are consistent with the MTT assay results showing anti-tumor cytotoxic action of apple stem cell extract treatments.

Example 12: Antioxidant Activity

The human body both produces and is subject to free radicals. Recovery of injury to any body tissue is frequently manifested by antioxidant enzyme levels. Superoxide anions are produced by dedicated signaling enzymes and as a byproduct of metabolism (e.g. mitochondrial respiration). Inhaled pathogens can also induce airway cells to produce these and other reactive oxidant species (ROS). For example, inhalation of the ubiquitous environmental fungus *Aspergillus fumigatus* can exacerbate airway inflammation. Inhaled ROS and those endogenously formed by inflammatory cells constitute an increased intrapulmonary oxidative burden. Despite their potential toxicity, superoxide ion and some of its derivatives, especially hydrogen peroxide ($H_2O_2$), are also signaling molecules that mediate a variety of biological responses such as cell proliferation, differentiation, and migration. The enzymes involved in repair of free radical-induced DNA damage may be especially important in preventing cancerous transformation.

When produced in excess, free radicals and oxidants generate oxidative stress, a deleterious process that can seriously alter cell membranes and other structures such as proteins, lipids, lipoproteins, and deoxyribonucleic acid. Free radicals, especially superoxide, and non-radicals, such as $H_2O_2$, can be generated in quantities large enough to overwhelm endogenous protective enzyme systems, such as superoxide dismutase (SOD), catalase (CAT), and reduced glutathione. The balance between oxidants and antioxidants (known as redox balance) is altered in many diseases with severe consequences. The pathophysiological mechanisms by which free radicals generate various types of stress (oxidative stress, nitrative, carbonyl, inflammatory, endoplasmic reticulum stress etc.) culminate in diseases such as chronic obstructive pulmonary disease, bronchial asthma, bronchiectasis, and idiopathic pulmonary fibrosis. Studies have shown that there is induction of SOD and CAT in inflamed tissues generally and in inflammatory lung diseases.

The endogenous antioxidant defense system is essential to maintain redox balance. Human tissue produces enzymes that protect against free radicals and ROS. The SOD enzyme helps convert superoxides to $H_2O_2$. $H_2O_2$ may be metabolized by other enzymes such as CAT and glutathione peroxidase. Overexpression of CAT has been associated with impaired post-ischemic neovascularization; this response of elevated anti-oxidant enzymes, though necessary to combat oxidative stress, has detrimental secondary consequences to tissue recovery and repair.

Measuring the antioxidant activity of an exemplary treatment extract of the invention illustrates whether the extract can exert a protective antioxidant effect. The assays below provide strongly oxidizing environments though addition or generation of an oxidizer (a superoxide radical in the SOD assay and $H_2O_2$ in the CAT assay). Addition of different concentrations of apple stem cell extract (see Example 1) may neutralize or inactivate part or all of the oxidizing material. Residual (unneutralized) oxidizer in the assays react with other reagents in the mixtures to provide a measurable absorbance proportional to the amount of remaining oxidizer. The loss of absorbing material (compared to a control with no ASC added) is a measure of the antioxidant activity of the ASC. Values close to zero show low antioxidant activity. Values close to 100% show full neutralization of the oxidizer and hence a stronger antioxidant activity. Higher values indicate a protective antioxidant potential of the plant stem cell extract.

These assays are labeled SOD and CAT because they measure antioxidant activity associated with these enzymes, if present. The assay results do not speak to the antioxidation mechanism. The ASC extract may include active antioxidant enzymes, other antioxidants, such as ascorbate or tocopherol, or combinations of these and other antioxidant materials.

Method: The SOD assay generates a superoxide radical of riboflavin that reacts with hydroxylamine hydrochloride to form nitrite. The nitrite reacts with sulphanilic acid in a Griess reagent to produce a diazonium compound which subsequently reacts with naphthylamine to produce a red azo compound with absorbance measured at 543 nm. In the assay, 100 μL aliquots of diluted ASC extract in a range of concentrations were each combined with 1.4 mL of an assay buffer (50 mM Phosphate buffer, pH 7.4, 20 mM L-Methionine, 1% (v/v) Triton X-100, 10 mM hydroxylamine, and 50 mM EDTA) and 80 μL of a stock riboflavin solution. Absorbance of triplicates were measured at 543 nm after addition of the Griess reagent.

CAT is a ubiquitous antioxidant enzyme that degrades hydrogen peroxide into water and oxygen. The CAT assay method is based on the principle that dichromate in acetic acid is reduced to chromic acetate when heated in the presence of $H_2O_2$. Hydrogen peroxide concentration is directly proportional to the concentration of chromic acetate produced as measured by absorbance at 610 nm. Antioxidants in different concentrations of ASC extracts in the assay preparation was allowed to degrade $H_2O_2$ for a fixed period. The reaction was stopped by the addition of dichromate/acetic acid mixture and the remaining $H_2O_2$ was determined by measuring chromic acetate colorimetrically after heating the reaction.

Results: superoxide radical inactivation in apple stem cell extracts at various concentrations. The assay was performed in triplicate, but the first replicate in each series was discarded due to an apparent systematic error. The remaining replicates for each concentration were averaged and the difference in average absorbance between each concentration and the control (no ASC) were divided by the absorbance of the control tubes. The final values, expressed as a percentage, indicate the fraction of the total superoxide radical deactivated.

Figure 13:
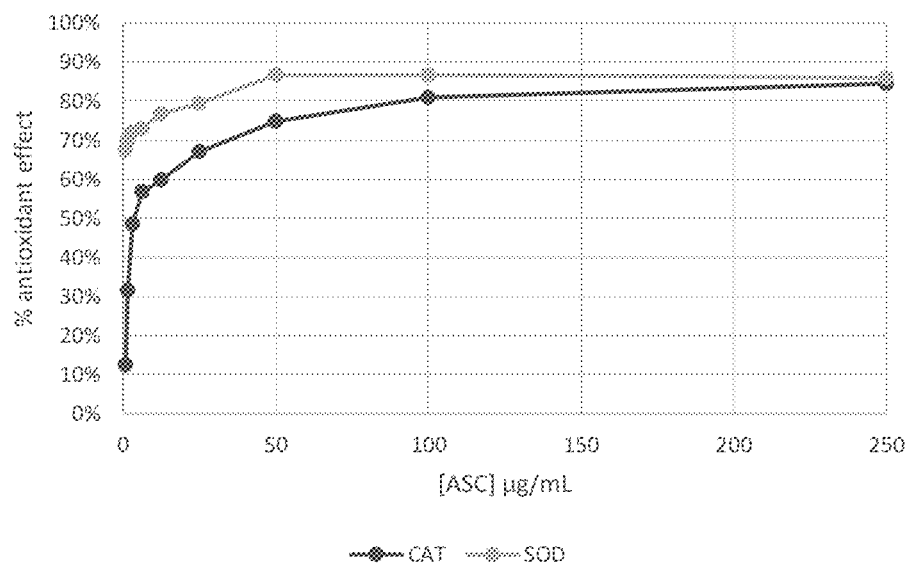

The mean percent inactivation of superoxide radical as compared to a no-ASC control is presented Table 24 and in FIG. 13. The inactivation monotonically increased with increasing concentrations of ASC. At concentrations of 50, 100 and 250 μg/mL ASC, the effect essentially saturated, probably limited by the assay conditions as evidenced by the very steep slopes at low ASC concentration. The data suggest that the ASC can protect against oxidative damage due to superoxide radicals.

TABLE 24

Oxidation protection of ASC treated cells as measured by SOD assay.

| superoxide radical inactivation ASC concentration (μg/mL) | Mean % (duplicates) |
| --- | --- |
| 250 | 0.087 |
| 100 | 0.083 |
| 50 | 0.083 |
| 25 | 0.128 |
| 12.5 | 0.145 |
| 6.25 | 0.169 |
| 3.125 | 0.175 |
| 1.562 | 0.186 |
| 0.871 | 0.203 |

Reported values are means of duplicates ratioed to control (no ASC).

Results: $H_2O_2$ inactivation. Peroxide inactivation was also measured in apple stem cell extracts at various concentrations. The assay was performed in triplicate to determine the antioxidant potential of apple stem cell extracts at various concentrations. The inactivation monotonically increased with increasing concentrations of ASC. At concentrations of 50, 100, and 250 μg/mL ASC, the antiperoxide effect flattened, probably limited by the assay conditions as evidenced by the very steep slopes at low ASC concentration. The data suggest that the ASC can protect against oxidative damage due to $H_2O_2$. The mean percent inactivation of $H_2O_2$ is presented in Table 25 and in FIG. 13.

TABLE 25

Oxidation protection of ASC treated cells as measured by CAT assay.

| $H_2O_2$ inactivation ASC concentration (μg/mL) | mean % (triplicates) |
| --- | --- |
| 250 | 85% |
| 100 | 81% |
| 50 | 75% |
| 25 | 67% |
| 12.5 | 60% |
| 6.25 | 57% |
| 3.125 | 48% |
| 1.562 | 31% |
| 0.781 | 12% |

Reported values are means of triplicates ratioed to control (no ASC).

The results show apple stem cell extracts can inactivate superoxide radicals and $H_2O_2$. This antioxidant activity suggests the materials may have value in treatment of pathologies including lung pathologies arising from or exacerbated by reactive oxygen species.

Plant SC products have thus been shown to be effective agents for multiple effects. There is variation in the efficacy between stem cell types and effects. ASC are more effective at selective cytotoxicity of lung cancer cells and LST and OSC are more effective in scratch assay recovery. Some of these differences may be attributable to concentration effects, but others may be attributable to a different mix of materials present in the different cell types. Non-stem cell extracts have some effects also, but the experiments indicate that the strong beneficial effects are associated with plant SC products.

The embodiments described herein are referred in the specification as "one embodiment," "an embodiment," "an example embodiment," etc. These references indicate that the embodiment(s) described can include a particular feature, structure, or characteristic, but every embodiment does not necessarily include every described feature, structure, or characteristic. Further, when a particular feature, structure, or characteristic is described in connection with an embodiment, such feature, structure, or characteristic in may also be used in connection with other embodiments whether or not explicitly described. Further, where specific examples are given, the skilled practitioner may understand the particular examples as providing particular benefits such that the invention as illustratively disclosed herein suitably may be practiced in the absence of any element which is not specifically disclosed herein or within that particular example.

This disclosure mentions certain other documents incorporated by reference. Where such documents conflict with the express disclosure of this document, this document shall control.

It will be apparent to those of ordinary skill in the art that many modifications and variations of the described embodiment are possible in the light of the above teachings without departing from the principles and concepts of the disclosure as set forth in the claims.

Although the present disclosure describes certain exemplary embodiments, it is to be understood that such disclosure is purely illustrative and is not to be interpreted as limiting. Consequently, without departing from the spirit and scope of the disclosure, various alterations, modifications, and/or alternative applications of the disclosure will, no doubt, be suggested to those skilled in the art after having read the preceding disclosure. Accordingly, it is intended that the following claims be interpreted as encompassing all alterations, modifications, or alternative applications as fall within the true spirit and scope of the disclosure.

We claim:

1. A system for treating a lung condition, the system comprising:
   a plant stem cell product, wherein the plant stem cell product includes an apple stem cell product; and
   an aerosolizing device configured to create an aerosol from the plant stem cell product and to deliver the aerosol to the lungs via inhalation.

2. The system of claim 1, wherein the apple stem cell includes one or more of a plant stem cell extract, a lyophilized plant stem cell, a plant stem cell enriched medium, or an intact plant stem cell.

3. The system of claim 2, wherein the apple stem cell is derived from a dedifferentiated cell of an apple plant.

4. The system of claim 3, wherein the dedifferentiated cell is derived from one or more of a stem, a meristem, a leaf, a flower, a fruit, a seed, a root, or a callus of the apple plant.

5. The system of claim 2, wherein the plant stem cell product further includes an excipient.

6. The system of claim 5, wherein the excipient includes one or more of lactose, mannose, sodium chloride, a phospholipid, a poly lactic acid, poly(lactic-co-glycolic acid), glycerol, a glycol, a surfactant, a xanthan gum, or a liposome.

7. The system of claim 2, wherein the plant stem cell product is encapsulated.

8. The system of claim 5, wherein the apple stem cell product is an apple stem cell.

9. The system of claim 8, wherein the apple stem cell product is an apple stem cell extract prepared by encapasulating a lysate of cultured apple stem cells in a liposome comprising a phospholipid, glycerin, and xanthan gum.

10. The system of claim 9, wherein the aerosolizing device is an electronic-cigarette.

11. The system of claim 1, wherein the aerosolizing device is a nebulizer, pressurized metered-dose inhaler, a personal vaporizer, a humidifier, a powder inhaler, a personal diffuser, a traditional cigarette, or an electronic-cigarette.

* * * * *